US009724328B2

(12) United States Patent
Ioannou et al.

(10) Patent No.: US 9,724,328 B2
(45) Date of Patent: Aug. 8, 2017

(54) METHODS AND COMPOSITIONS FOR TREATMENT OF LIPID STORAGE DISORDERS

(71) Applicants: NEUROTROPE BIOSCIENCE, Newark, NJ (US); THE MOUNT SINAI HOSPITAL, New York, NY (US)

(72) Inventors: Yiannis A. Ioannou, New York, NY (US); Lawrence Altstiel, Stonington, CT (US); David R. Crockford, Newburyport, MA (US); Sathapana Kongsamut, Madison, NJ (US)

(73) Assignees: Icahn School of Medicine at Mount Sinai, New York, NY (US); Neurotrope Bioscience, Newark, NJ (US)

( * ) Notice: Subject to any disclaimer, the term of this patent is extended or adjusted under 35 U.S.C. 154(b) by 0 days.

(21) Appl. No.: 14/686,711

(22) Filed: Apr. 14, 2015

(65) Prior Publication Data
US 2015/0297559 A1    Oct. 22, 2015

Related U.S. Application Data

(60) Provisional application No. 61/981,473, filed on Apr. 18, 2014, provisional application No. 61/987,360, filed on May 1, 2014.

(51) Int. Cl.
A61K 31/366     (2006.01)
A61K 31/365     (2006.01)
A61K 31/215     (2006.01)
A61K 31/00      (2006.01)

(52) U.S. Cl.
CPC .......... A61K 31/366 (2013.01); A61K 31/215 (2013.01); A61K 31/365 (2013.01); A61K 31/00 (2013.01)

(58) Field of Classification Search
CPC .................................................. A61K 31/366
USPC ................................................. 514/451, 460
See application file for complete search history.

(56) References Cited

U.S. PATENT DOCUMENTS 6,624,189 B2   9/2003  Wender et al.
7,256,286 B2   8/2007  Wender et al.
8,163,800 B2   4/2012  Nelson et al.
8,497,385 B2   7/2013  Wender
(Continued)

FOREIGN PATENT DOCUMENTS

WO   WO 2009/099563 A2   8/2009
WO   WO 2010/014585 A1   2/2010
WO   WO 2015/148975 A1   10/2015

OTHER PUBLICATIONS

Tamari et al, "PKC Activation in Neimann Pick C1 Cells Restores Subcellular Cholesterol Transport," PLOS:One; Received Apr. 15, 2013 and published Aug. 15, 2013, pp. 1-12.*
(Continued)

Primary Examiner — Kamal Saeed
Assistant Examiner — Janet L Coppins
(74) Attorney, Agent, or Firm — Cooley LLP; Ivor R. Elrifi; Heidi A. Erlacher

(57) ABSTRACT

Treating subjects having a lipid storage disorder with a composition comprising a PKC activator, such as bryostatins, bryologs, and polyunsaturated fatty acids.

20 Claims, 17 Drawing Sheets

(56) References Cited

U.S. PATENT DOCUMENTS

2011/0196028 A1    8/2011   Etcheberrigaray et al.
2012/0156180 A1    6/2012   Bongarzone

OTHER PUBLICATIONS

Azzi, et al. "The Protein Kinase C Family," Eur. J. Biochem. 208, 547-557 (1992).

Bertrand, et al. "Phosphorylation of vimentin is an intermediate step in protein kinase C-mediated glycoconjugate secretion," American Physiological Society C611-C621 (1994).

Bolard, "How do the polyene macrolide antibiotics affect the cellular membrane properties?" Biochimica et Biophysica Acta 864 (1986) 257-304.

Chen, et al. "NPC1 late endosomes contain elevated levels of non-esterified ('free') fatty acids and an abnormally glycosylated form of the NPC2 protein," Biochem. J. (2005) 390, 549-561.

Cloud-Heflin, et al. "Expression, subcellular distribution and response to phorbol esters of protein kinase C (PKC) isozymes in drug-sensitive and multidrug-resistant KB cells," Eur. J. Biochem. 239, 796-804 (1996).

Disatnik, et al. "Localization of Protein Kinase C Isozymes in Cardiac Myocytes," Experimental Cell Research 210, 287-297 (1994).

Eriksson, et al. "Specific in vivo phosphorylation sites determine the assembly dynamics of vimentin intermediate filaments," Journal of Cell Science 117, 919-932 (2004).

Garver, et al. "The *Npcl* mutation causes an altered expression of caveolin-1, annexin II and protein kinases and phosphorylation of caveolin-1 and annexin II in murine livers," Biochimica et Biophysica Acta 1453 (1999) 193-206.

Goldin, et al. "Type C Niemann-Pick disease: A murine model of the lysosomal cholesterol lipidosis accumulates sphingosine and sphinganine in liver," Biochimica et Biophysica Acta 117 (1992), 303-311.

Higgins, et al. "Niemann-Pick C1 is a Late Endosome-Resident Protein That Transiently associates with Lysosomes and the Trans-Golgi Network," Molecular Genetics and Metabolism 68, 1-13 (1999).

Ioannou, et al., "Fabry Disease: Preclinical Studies Demonstrate the Effectiveness of x-Galactosidase A Replacement in Enzyme-Deficient Mice," Am. J. Hum., Genet. 68: 14-25, (2001).

Ioannou, "Defects in transmembrane proteins," Oxford University Press 206-228 (2004).

Ivaska, et al. "PKCε-mediated phosphorylation of vimentin controls integrin recycling and motility," The EMBO Journal (2005) 24, 3834-3845.

Kanno, et al. "The linoleic acid derivative DCP-LA selectively activates PKC-ε, possibly binding to the phosphatidylserine binding site," Journal of Lipid Research, vol. 47, 1146-1156 (2006).

Khan, et al. "Selective Regulation of Protein Kinase C Isoenzymes by Oleic Acid in Human Platelets," The Journal of Biological Chemistry, vol. 268, No. 7, 5063-5068 (1993).

Kim, et al. "Diazoxide acts more as a PKC-εactivator, and indirectly activates the mitochondrial $K_{ATP}$ channel conferring cardioprotection against hypoxic injury," British Journal of Pharmacology (2006) 149, 1059-1070.

Klymkowsky, "Intermediate Filament Organization, Reorganization, and Function in the Clawed Frog *Xenopus*," Current Topics in Developmental Biology, vol. 31, 455-486 (1995).

Leventhal, et al. "Suppression of Macrophade Eicosanoid Synthesis by Atherogenic Lipoproteins Is Profoundly Affected by Cholesterol-Fatty Acyl Esterification and the Niemann-Pick C Pathway of Lipid Trafficking," The Journal of Biological Chemistry, vol. 279, No. 9, 8084-8092, (2004).

Mangoura, et al. "Phorbol esters and PKC signaling regulate proliferation, vimentin cytoskeleton assembly and glutamine synthetase activity of chick embryo cerebrum astrocytes in culture," Developmental Brain Research 87 (1995) 1-11.

Mellor, et al. "The extended protein kinase C superfamily," Biochem. J. (1998) 332 281-292.

Millard, et al. "Niemann-Pick Type C1 (NPC1) Overexpression Alters Cellular Cholesterol Homeostatis," The Journal of Biological Chemistry, vol. 275, No. 49, 38445-38451 (2000).

Mochly-Rosen, et al. "Protein kinase C, an elusive therapeutics target?" *Nat Rev Drug Discov.* Dec. 2012; 11(12): 937-957.

Mor-Vaknin, et al. "Vimentin is secreted by activated macrophages," Nature Cell Biology, vol. 5, 59-63 (2003), and Supplementary Information, 3 pages.

Nishizuka, "Intracellular Signaling by Hydrolysis of Phospholipids and Activation of Protein Kinase C," Science, vol. 258, 607-614 (1992).

Pentchev, et al., "A Genetic Storage Disorder in BALB/C Mice with a Metabolic Block in Esterification of Exogenous Cholesterol," The Journal of Biological Chemistry, vol. 259, No. 9, 5784-5791 (1984).

Perlson, et al., "Vimentin-Dependent Spatial Translocation of an Activated MAP Kinase in Injured Nerve," Neuron, vol. 45, 715-726, (2005).

Puri, et al., "Cholesterol modulates membrane traffic along the endocytic pathway in sphingolipid-storage diseases," Nature Cell Biology, vol. 1, 386-388 (1999).

Rodriguez-Lafrasse, et al., "Modulation of protein kinase C by endogenous sphingosine: inhibition of phorbol dibutyrate binding in Niemann-Pick C fibroblasts," Biochem. J. (1997) 325, 787-791.

Sarria, et al., "A Functional Role for Vimentin Intermediate Filaments in the Metabolism of Lipoprotein-derived Cholesterol in Human SW-13 Cells," The Journal of Biological Chemistry, vol. 267, No. 27, 19455-19463 (1992).

Shen, et al., "Ablation of Vimentin Results in Defective Steroidogenesis," Endocrinology, 2012, 153(7): 3249-3257.

Spudich, et al., "Association of the β Isoform of Protein Kinase C With Vimentin Filaments," Cell Motility and Cytoskeleton 22: 250-256 (1992).

Styers, et al., "Intermediate Filaments and Vesicular Membrane Traffic: The Odd Couple's First Dance?" Traffic (2005) 6, 359-365.

Szalay, et al., "Associations of PKC Isoforms with the Cytoskeleton of B16F10 Melanoma Cells," The Journal of Histochemistry & Cytochemistry, vol. 49(1): 49-65, (2001).

Tanaka, et al., "The Newly Synthesized Linoleic Acid Derivative FR236924 Induces a Long-Lasting Facilitation of Hippocampal Neurotransmission by Targeting Nicotinic Acetylcholine Receptors," Bioorganic & Medicinal Chemistry Letters 13 (2003) 1037-1040.

Toda, et al., "Evidence That Formation of Vimentin-Mitogen-activated Protein Kinase (MAPK) Complex Mediates Mast Cell Activation following FceRI/CC Chemokine Receptor 1 Cross-talk," J. Biol. Chem. Jul. 13, 2012; 287(29): 24516-24524.

Walter, et al., "Telomerase immortalization upregulates Rab9 expression and restores LDL cholesterol egress from Niemann-Pick C1 late endosomes," Journal of Lipid Research, vol. 44, 243-253 (2003).

Walter, et al., "Endosomal lipid accumulation in NPC1 leads to inhibition of PKC, hypophosphorylation of vimentin and Rab9 entrapment," Biol. Cell (2009) 101, 141-152.

Anonymous, "Neurotrope Enters Collaborative Agreement with Icahn School of Medicine at Mount Sinai for use of Bryostatin-1 in the Treatment of Niemann-Pick Disease Type C", Jul. 22, 2014, PR Newswire, www.finanznachrichten,de, pp. 1-3.

\* cited by examiner

Figure 5
A
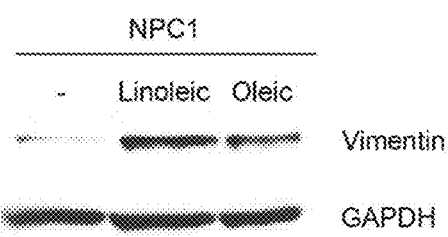
B
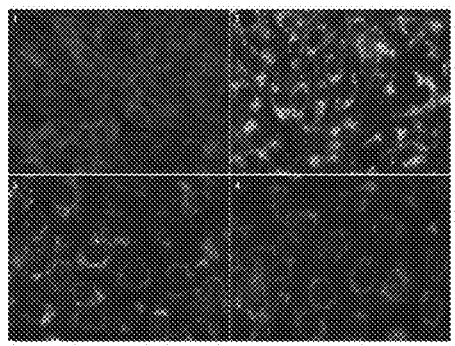
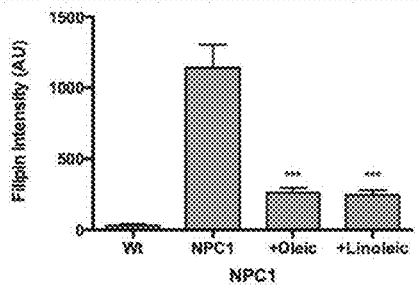
C
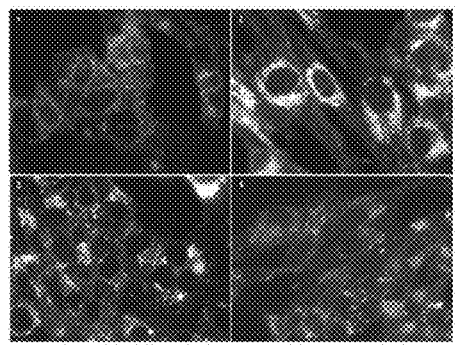
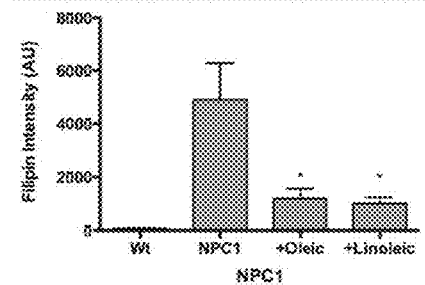

METHODS AND COMPOSITIONS FOR TREATMENT OF LIPID STORAGE DISORDERS

PRIORITY CLAIM

This application claims priority to U.S. provisional patent application No. 61/981,473 filed Apr. 18, 2014 and U.S. provisional patent application No. 61/987,360 filed May 1, 2014, the contents of which are expressly incorporated by reference.

STATEMENT OF GOVERNMENT INTEREST

This invention was made with government support under Grant RO1DK082712 awarded by National Institute of Health. The government has certain rights in the invention.

BACKGROUND

All references cited herein are expressly incorporated by reference.

Lipid storage disorders (or lipidoses) are a group of inherited metabolic disorders in which harmful amounts of lipids accumulate in some of the body's cells and tissues. People with these disorders generally either do not produce enough of one of the enzymes needed to metabolize lipids or they produce enzymes that do not work properly. Over time, this excessive storage of fats can cause permanent cellular and tissue damage.

Many lipid storage disorders lack adequate therapeutics for treatment. These disorders include, for example, Niemann-Pick disease types A, B and C, Gaucher disease Type II, Fabry disease (note that an enzyme replacement is available), gangliosidoses including Tay-Sachs disease, Sandhoff disease, Krabbe disease, Metachromatic leukodystrophy, and cholesteryl ester storage disease (Wolman's disease).

Niemann-Pick disease is an inherited autosomal recessive lipid storage disorder characterized by excessive accumulation of sphingomyelin in the lysosomes of cells such as macrophages and neurons, which impairs normal cellular function. Niemann-Pick Type A results from a deficiency of acid sphingomyelinase and is a rapidly progressive neurodegenerative disease. It typically results in death within two to three years of age. Niemann-Pick Type B is a milder form that results in the enlargement of the liver and spleen, and respiratory distress with death generally ensuing by early adulthood. These two forms of Niemann-Pick disease which are both associated with acid sphingomyelinase (ASM) deficiencies are referred to collectively herein as Niemann-Pick disease, or ASM deficiency (ASMD). Other types of Niemann-Pick disease, e.g., Type C, do not involve mutations in the ASM gene and are not directly attributable to the function of ASM. The nature of the biochemical and molecular defects that underlie the remarkable clinical heterogeneity of the A and B subtypes remains unknown. Although patients with both subtypes have residual ASM activity (about 1 to 10% of normal), biochemical analysis cannot reliably distinguish the two phenotypes. Moreover, the clinical course of Type B NPD is highly variable, and it is not presently possible to correlate disease severity with the level of residual ASM activity.

Niemann-Pick Type C is results from mutations in NPC1 and NPC2 genes. In Niemann-Pick Type C, the protein product of the major mutated gene NPC1 is not an enzyme but appears to function as a transporter in the endosomal-lysosomal system, which moves large water-insoluble molecules through the cell. The protein coded by the NPC2 gene has been shown to be a small cholesterol-binding protein that resides in the lysosome lumen. The disruption of this transport system results in the accumulation of cholesterol and glycolipids in lysosomes.

Niemann Pick disease, as well as other lipid storage disorders, is a disorder for which there remains an overwhelming need for therapeutics for treatment. Presently there is no FDA approved therapy for Neimann Pick disease in the United States; and treatments for this disease are limited with most people afflicted with Type A dying by age 18 months, while those with Type B or Type C, frequently live into their teenage years.

SUMMARY

The protein kinase C (PKC) family of enzymes is responsible for a multitude of cellular processes through the enzymes' ability to regulate proteins via signal transduction cascades. The members of this kinase family are structurally and functionally similar and are categorized into conventional ($\alpha$, $\beta I$, $\beta II$ and $\gamma$), novel ($\delta$, $\epsilon$, $\eta$, and $\theta$), and atypical isoforms ($\zeta$ and $\lambda$). These isoforms have been implicated in a variety of diseases and pathological conditions.

The present disclosure is based in part on the previously unappreciated role for PKCs in lipid storage disorders such as Niemann-Pick Type C (NPC1) disease. We observed that the intermediate filament, vimentin, is hypophosphorylated in NPC1 cells compared to wild-type (WT) cells and that this hypophosphorylation results from reduced activity [5]. Vimentin is involved in a variety of cellular processes, including vesicular membrane transport [6,7], signal transduction [8,9] and cell motility [10]. Similar to NPC1 cells, cells lacking vimentin are unable to transport LDL-derived cholesterol from their lysosomes to the endoplasmic reticulum for esterification [11]. The decreased vimentin phosphorylation in NPC1 cells reduces the pool of soluble vimentin, likely disrupting the vimentin cycle, which is necessary for transport to take place [12, 13]. Vimentin has been shown to be phosphorylated by several proteins, including the PKCs [14] and in particular the $\alpha$ [15], $\epsilon$ [10] and $\beta II$ [16, 17] isoforms.

Accordingly, the present disclosure provides methods for treating human subjects suffering from lipid storage disorders, such as Niemann-Pick disease, by administering PKC activators.

The present disclosure provides, according to certain embodiments, methods comprising administering to a subject with a lipid storage disorder a pharmaceutically effective amount of a PKC activator.

The present disclosure provides, according to certain embodiments, methods comprising administering to a subject with Niemann-Pick Type C disease a pharmaceutically effective amount of bryostatin 1.

The features and advantages of the present disclosure will be readily apparent to those skilled in the art upon a reading of the description of the embodiments that follows.

DRAWINGS

Some specific embodiments of the disclosure may be understood by referring, in part, to the following description and the accompanying drawings.

FIG. 1 is a Western blot showing the effects of transient PKC expression on vimentin solubilization in human NPC1 cells. Representative Western blot analyses of soluble and insoluble vimentin levels in human NPC1 3123 (panel A) and human nullNPC1o (panel B) cells transfected with PKC ε, β, or α show that the three isoforms increase levels of soluble vimentin and Rab9 with a concurrent decrease of insoluble vimentin relative to untransfected cells (−). The levels of vimentin solubilized are similar to that seen in cells expressing Rab9 (Rab9). The blots shown are representative of at least 3 independent experiments.

FIG. 2 is a Western blot showing Rab9 release from insoluble vimentin fraction of NPC1 cell lysates. The insoluble vimentin fraction from NPC1 cell lysates was incubated with various PKC isoforms. All isoforms tested can affect Rab9 release to some degree from the insoluble vimentin fraction, with PKCα being the most effective and PKCγ being the least effective. The blots shown are representative of at least 3 independent experiments.

FIG. 3 is a graph showing the effects of PKCs and fatty acids on cholesterol esterification in M12 NPC1 CHO cells. M12 cells were treated with 50 μg/ml fatty acids for 2 days and then transfected with the indicated PKC isoforms. Following transfection, cholesterol transport was assessed by esterification assay. Both free fatty acids and PKCs alleviate the cholesterol transport defect of NPC1 cells and their effects appear to be additive.

FIG. 4 are images showing the effects of transient PKC expression on the NPC1 phenotype. M12 cells were transfected with PKC isoforms or Rab9 for 48 hrs and then analyzed by filipin staining for cholesterol storage. Cells positive for transfection stain positive for GFP (left panel) and show decreased filipin staining (outlined cells, right panel) compared to surrounding untransfected cells, confirming the role of PKCs in mobilizing stored cholesterol from the NPC1 endosomes. Bar, 20 μm.

FIG. 5 shows the effects of fatty acids on vimentin solubilization and the NPC1 phenotype. (A) Human NPC1 3123 cells were treated with 50 μg/ml linoleic or oleic acid for 24 hrs, after which the levels of soluble vimentin were analyzed by Western blotting. Cholesterol storage in NPC1 CHO (B) or human 3123 (C) cells was analyzed by filipin staining. Fluorescence intensity was quantitated in at least 150 cells for each sample. The bar graph represents average values±SEM from 3 independent experiments. * and *** denote statistically significant differences between treated and untreated cells with $P<0.05$ and $P<0.0001$, respectively, as determined by Student's t-test.

FIG. 6 shows the effects of PKC activation on the NPC1 phenotype. NPC1 CHO cells (B through F) were treated with 100 μM DCP-LA (C), 10 μM DHA (D), or 100 μM diazoxide (E) and cholesterol storage was quantified by filipin fluorescence. WT CHO cells are shown in (A). Filipin intensity was quantitated in at least 150 cells for each sample. The bar graph represents average values±SEM from 3 independent experiments. *, , and * denote statistically significant differences between treated and untreated cells with $P<0.05$, $P<0.01$ and $P<0.0001$, respectively, as determined by Student's t-test.

FIG. 7 are images showing the effects of PKC activation on sphingolipid transport. Human NPC1 3123 cells were treated with (B) 20 μM DCP-LA, (C) 2 μg/ml oleic acid, (D) 2 μg/ml linoleic acid, or (F) 100 nM PMA for 48 hours before BODIPY-LacCer staining was performed. In untreated cells (A), transport of the lipid to the trans-Golgi network (TGN) is inhibited and staining is visible only in punctate endocytic vesicles. In contrast, in treated cells the lipid can be seen in the TGN (arrows) in treated cells, indicating release of the transport block that characterizes NPC1.

Figure 1:
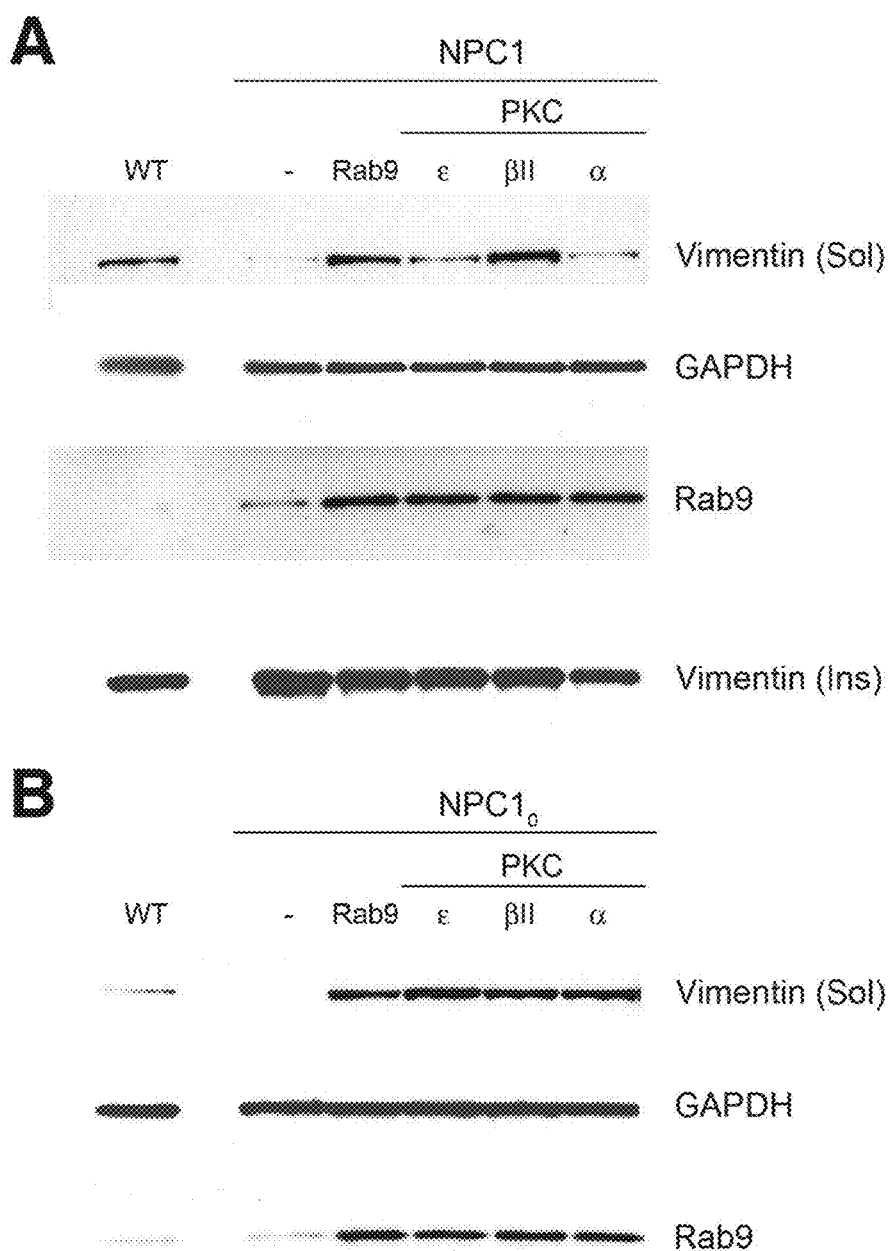

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

In general, the present disclosure provides methods for treating lipid storage disorders using PKC activators. As used herein, "protein kinase C activator" or "PKC activator" refers to a substance that increases the rate of the reaction catalyzed by protein kinase C, upregulates the expression of PKC (e.g., upregulates the expression of PKCα, PKC βII, PKC γ and/or PKC ε), or otherwise facilitates the activation of PKC.

In certain embodiments, the present disclosure provides methods comprising administering to a human subject with a lipid storage disorder a pharmaceutically effective amount of a PKC activator. The PKC activator may be administered as part of a composition suitable for administration to a human subject.

In certain embodiments, the PKC activator may be any of bryostatin 1-20, a bryolog, neristatin, a polyunsaturated fatty acid, or a combinations thereof.

Bryostatins may be used in the methods of the present disclosure. The bryostatins are a family of naturally occurring macrocyclic compounds originally isolated from marine bryozoa. Currently, there are about 20 known natural bryostatins which share three six-membered rings designated A, B and C, and which differ mainly in the nature of their substituents at C7 ($OR^A$) and C20 ($R^B$).

Formula A

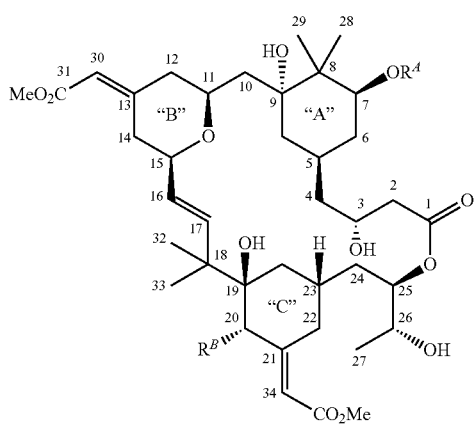

Bryostatin 1 and derivatives of bryostatin 1 are described in U.S. Pat. No. 4,560,774 (incorporated herein by reference). Examples of suitable bryostatins that may be used with the methods of the present disclosure include, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17 bryostatin 18, bryostatin 19, and bryostatin 20.

Analogs of bryostatins, commonly referred to as bryologs, also may be used in the methods of the present disclosure. Bryologs are structural analogues of bryostatin. While bryostatin has two pyran rings and one 6-membered cyclic acetal, in most bryologs one of the pyrans of bryostatin is replaced with a second 6-membered acetal ring. This modification reduces the stability of bryologs, relative to bryostatin, for example, in both strong acid or base, but has little significance at physiological pH. Bryologs also have a lower molecular weight (ranging from about 600 to 755), as compared to bryostatin (988), a property which may facilitate transport across the blood-brain barrier. Examples of suitable bryologs include, but are not limited to analogs and derivatives of bryostatins such as those disclosed in U.S. Pat. Nos. 6,624,189, 7,256,286 and 8,497,385 (the disclosures of which are incorporated herein by reference).

In certain embodiments, polyunsaturated fatty acid esters (PUFAs or polyenoic fatty acids)) may be used in the methods of the present disclosure for treating lipid storage disorders. A PUFA is a fatty acid containing more than one double bond. There are three classes of PUFAs, omega-3 PUFAs, omega-6 PUFAs, and omega-9 PUFAS. In omega-3 PUFAs, the first double bond is found 3 carbons away from the last carbon in the chain (the omega carbon). In omega-6 PUFAs the first double bond is found 6 carbons away from the chain and in omega-9 PUFAs the first double bond is 9 carbons from the omega carbon. As used herein, the term PUFA includes both naturally-occurring and synthetic fatty acids. A major source for PUFAs is from marine fish and vegetable oils derived from oil seed crops. Examples of PUFA's suitable for use in the methods of the present disclosure include, but are not limited to, esters of 8-[2-(2-pentyl-cyclopropylmethyl)cyclopropyl]-octanoic acid (DC-PLA), as well as those described in U.S. Pat. No. 8,163,800 and in PCT publication WO 2010014585 A1.

Another example of suitable PKC activators include potassium channel activators such as, for example, diazoxide.

In certain embodiments, neristatins, such as neristatin 1, may be used in the methods of the present disclosure for treating lipid storage disorders.

Other suitable PKC activators include, but are not limited to, phorbol-12-myristate-13-acetate (PMA), okadaic acid, 1α,25-dihydroxyvitamin D3, 12-deoxyphorbol-13-acetate (prostratin), 1,2-dioctanoyl-sn-glycerol (DOG), 1-oleoyl-2-acetyl-sn-glycerol (OAG), (2S,5S)-(E,E)-8-(5-(4-(trifluoromethyl)phenyl)-2,4-pentadienoylamino)benzolactam (α-amyloid precursor protein modulator), cis-9-octadecenoic acid (oleic acid), ingenol 3-angelate, resiniferatoxin, L-α-Phosphatidyl-D-myo-inositol-4,5-bisphosphate, triammonium salt (PIP2), phorbol-12,13-dibutyrate, 8(S-hydroxy-(5Z,9E,11Z,14Z)-eicosatetraenoic acid (8(S)-HETE), 12β-[(E,E)-5-Phenyl-2,4-pentadienoyloxy]daphnetoxin (merzerein), clomiphene citrate, sodium oleate, phorbol 12,13-diacetate, phorbol-12,13-didecanoate, 1,2-dipalmitoyl-sn-glycerol, 1-Stearoyl-2-linoleoyl-sn-glycerol, phorbol-12,13-didecanoate, 1,2-dipalmitoyl-sn-glycerol, 1-stearoyl-2-linoleoyl-sn-glycerol, phorbol 12,13-dihexanoate, prostratin and its analogs, resiniferonol 9,13,14-orthophenylacetate, C-8 ceramide, 1,6-bis(Cyclohexyloximinocarbonylamino)hexane; 1,6-Di(O-(carbamoyl) cyclohexanone oxime)hexane (RHC-80267), (+/−)-1-oleoyl-2-acetylglycerol, 5(S),6(R),15(S)-TriHETE (Lipoxin A4), (−)-Indolactam V, SC-9, SC-10, zoledronic acid monohydrate, 12-deoxyphorbo 13-angelate 20-acetate, 6-(N-decylamino)-4-hydroxymethylindole, 4α-phorbol 12,13-dibutyrate, 1,2-dihexanoyl-sn-glycerol, zoledronic acid disodium salt tetrahydrate, arachidonic acid methyl ester, arachidonic acid-d8.

As used herein, "a pharmaceutically effective amount" is an amount of a pharmaceutical compound or composition having a therapeutically relevant effect on a lipid storage disorder. A therapeutically relevant effect relates to some improvement in a biomechanical process (e.g., gait, use of limbs, and the like) or a change in the cellular, physiological or biochemical parameters associated with any of the causes of a particular lipid transport disorder (e.g., vimentin solubility, cholesterol esterification, cholesterol accumulation and transport, glycosphingolipid accumulation and transport).

In certain embodiments, a pharmaceutically effective amount for bryostatins and bryologs may be from about 0.0000001 to about 500 mg per kg host body weight per day, which can be administered in single or multiple doses. In some embodiments, the dosage level may be: from about 0.0000001 mg/kg to about 250 mg/kg per day; from about 0.0000005 mg/kg to about 100 mg/kg per day; from at least about 0.0000001 mg/kg to about 250 mg/kg per day; from at least about 0.00000005 mg/kg to about 100 mg/kg per day; from at least about 0.000001 mg/kg to about 50 mg/kg per day; or from about 0.00001 mg/kg to about 5.0 mg/kg per dose. In other embodiments, the dosage may be about 0.00000001 mg/kg to about 0.00005 mg/kg; 0.00005 mg/kg to about 0.05 mg/kg; about 0.0005 mg/kg to about 5.0 mg/kg per day; about 0.0001 mg/kg to about 0.5 mg/kg per dose; or 0.001 to 0.25 mg/kg per dose.

In certain specific embodiments, in which the lipid storage disorder is Niemann-Pick disease, a pharmaceutically effective amount of a PKC activator may be an amount sufficient to solubilize vimentin and/or release trapped Rab9.

In certain embodiments, the dosing is from about 1 μg/kg (3-25 μg/m$^2$) to 120 μg/kg (360-3000 μg/m$^2$). In other embodiments, the dosing is from about 0.04-0.3 μg/kg (1 μg/m$^2$) to about 1-10 μg/kg (25 μg/m$^2$). In other embodiments, the dosing is from about 0.01 μg/m$^2$ to about 25

μg/m². In other embodiments, the dosing is from about 0.0002-0.0004 μg/kg to about 0.05-1 μg/kg.

In certain embodiments, the PKC activator is a PUFA administered at a dosage of about 0.001 to 100 mg/kg; 0.01 to about 50 mg/kg; about 0.1 to about 10 mg/kg.

In certain embodiments, the PKC activator present in the compositions used in the methods of the present disclosure is a bryostatin or bryolog, and the bryostatin or bryolog is used in an amount from about 0.0001 to about 1000 milligrams. In some embodiments, the bryostatin or bryolog is used in an amount from at least about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, or about 1000.0 milligrams.

The compositions used in the methods of the present disclosure may be administered via any suitable route; for example, orally, intraperitoneally, subcutaneously, intranasally, buccally, trans-dermally intramuscularly, intrarectally, intravenously, and by oral inhalation.

The compositions used in the methods of the present disclosure may be administered on a regimen of 1 to 4 times per day, and in some embodiments, the compositions are administered twice a week, once a week, once every two weeks, once every three weeks, once every four weeks, once every six weeks, once every eight weeks or even less frequently depending on the needs of the patient.

The compositions used in the methods of the present disclosure may be administered as part of a course of treatment lasting for about 1 to about 30 days; about 1 to about 90 days; about 1 to about 120 days; about 1 to about 180 days; about 1 to 365 days; one year; two years; three years; or for the patient's lifetime.

It will be understood, however, that the specific dose level and frequency of dosage for any particular host may be varied and will depend upon a variety of factors including the activity of the specific compound employed, the metabolic stability and length of action of that compound, the age, body weight, general health, sex, diet, mode and time of administration, rate of excretion, drug combination, the nature of the disorder, the severity of the particular disorder, and the host undergoing therapy.

To facilitate a better understanding of the present invention, the following examples of specific embodiments are given. In no way should the following examples be read to limit or define the entire scope of the invention

EXAMPLES

Example 1

Materials and Methods

Dulbecco's Modified Eagle Medium (DMEM), trypsin, L-glutamine, gentamicin, and NuPage gels and buffers were obtained from Invitrogen (Carlsbad, Calif.) while FBS was from Hyclone, Thermo Scientific (Rockford, Ill.). The monoclonal anti-vimentin (V9), conjugated anti-mouse-IgG and anti-rabbit-IgG antibodies were from Santa Cruz Biotechnologies, Inc. (Santa Cruz, Calif.). The anti-GAPDH antibody was from Millipore (Billerica, Mass.) and the anti-Rab9 polyclonal antibody has been described elsewhere [27]. Filipin was from Polysciences, Inc. (Warrington, Pa.). Lumilight Plus substrate and FuGENE™ 6 transfection reagent were both from Roche Diagnostics (Indianapolis, Ind.). [9,10-3H(N)] oleic acid (15 Ci/mmol) was obtained from NEN Life Science Products (Boston, Mass.) and LDL was from EMD Biosciences Inc. (La Jolla, Calif.). All other chemicals were acquired from Sigma-Aldrich (St. Louis, Mo.).

Cell Culture and Transfection

The human wild-type fibroblast (GM05387), NPClo fibroblast (GM09341), and NPC1 fibroblast (GM03123) cell lines were obtained from Coriell Cell Repositories (Camden, N.J.). The M12 Chinese hamster ovary (CHO) cell line and its wild-type parental line were obtained and cultured. Fibroblast cell lines were cultured in DMEM, and CHO cells were cultured in DMEM/F12 (50:50) medium, supplemented with 10% FBS, 2 mM L-glutamine, and 50 μg/ml gentamicin in a humidified incubator at 37° C. with 5% $CO_2$.

The cDNA for PKC α was cloned into the bicistronic vector pIRES (Stratagene), which contains GFP for monitoring successful transfection. The cDNAs for PKC βII, and PKC ε (ATCC) were cloned into vector pYDual, which expresses a nuclear-targeted RFP (Ioannou, unpublished). A Rab9-YFP fusion construct (described in [5]) was used for Rab9 expression. Transient overexpression was achieved by transfecting cells at 70% confluency using the FuGENE™ 6 reagent (Roche Diagnostics) according to the manufacturer's suggestions.

Protein Analyses

Transfected cells were harvested with PBS containing 2 mM EDTA at 2 days post-transfection. Soluble and insoluble cell fractions were prepared as described previously [5]. Briefly, to obtain the soluble/cytoplasmic fraction, cells were incubated on ice for 30 min in cold "phospho" buffer [150 mM NaCl, 20 mM NaF, 100 μM $Na_3VO_4$, 20 mM Hepes, pH 7.5), 1% (v/v) Igepal, 10% (v/v) glycerol, and 1 μL/20 mg tissue of protease inhibitor cocktail] and then centrifuged for 20 min at 14,000 rpm at 4° C.; the clear supernatant was frozen in aliquots at a concentration of 1 μg/μl. The pellet (insoluble fraction) was washed 3 times in ice-cold PBS containing 2 mM EDTA and then resuspended in a volume of "Triton" buffer [PBS, 1% (w/v) SDS, and 0.1% (v/v) Triton X-100] equal to the "phospho" buffer. This solution was boiled for 10 min and sonicated until the solution became clear. The protein concentration of this fraction was adjusted to 1 μg/μl according to the protein concentrations determined for the soluble/cytoplasmic fraction. Protein concentrations were determined using the fluorescamine method as we have described [36]. 4-12% Bis-Tris precast gel (Invitrogen, Carlsbad, Calif.) and then transferred onto a Protran membrane using an XCell II apparatus (Invitrogen, Carlsbad, Calif.) according to the manufacturer's instructions. Blots were processed as described previously [27].

For Rab9 dissociation studies, 1.0×10⁷ NPC1 3123 cells were collected in ice-cold PBS and lysed by sonication 4 times for 10 s each. The lysate was centrifuged at 14,000 rpm for 10 minutes to separate the soluble from the insoluble fractions and the total protein concentration was determined using a modified Bradford assay (Bio-Rad, Hercules, Calif.). An equal amount of each insoluble fraction was mixed with each purified PKC isoform from a PKC isozyme panel (Sigma, St. Louis, Mo.) and incubated for 60 min at 37° C. An equal volume of each sample was resolved through a 4-12% Bis-Tris precast gel, transferred to a membrane, and processed as described above.

Cholesterol Esterification

The preparation of [³H] oleate substrate and esterification assays were performed as previously described [5]. Cells were treated with 50 μg/ml fatty acid for 2 days and then transfected with PKE α or PKC ε for 24 hrs before esterification assays. All values were generated in triplicate and normalized for total cell protein.

Immunofluorescence Microscopy

For filipin staining in transfected cells, cells were transfected with PKC or Rab9 using Fugene 6 according to the manufacturer's recommendations. After 48 hrs, cells were stained with filipin as we have previously described [37]. Cells were mounted onto slides using Fluoromount-G (SouthernBiotech, Birmingham, Ala.) and analyzed on a Nikon Eclipse microscope fitted with a charge-coupled-device camera (Nikon, Melville, N.Y.). Images were acquired with MetaVue software and then deconvoluted using AutoDeblur software from AutoQuant Imaging, Inc (Troy, N.Y.). For quantitation of filipin fluorescence, cells were seeded at $3\times10^5$ cells/well in 6-well dishes and allowed to settle overnight, after which the medium was replaced with medium containing 10% lipoprotein deficient serum (LPDS) for 4 days. Cells were incubated with oleic/linoleic acids for 48 hours, DCPLA/DHA for 24 hrs, or diazoxide for 72 hrs before fixing and staining with filipin as we have previously described. Images were acquired using the same exposure time for all samples. Fluorescence intensity was determined using the integrated intensity function of MetaVue software; at least 150 cells were quantitated for each sample and each experiment was repeated 3 times. For analysis of sphingolipid transport, cells were incubated with oleic/linoleic acids, DCP-LA, or PMA for 48 hours before BODIPY-LacCer staining was performed as previously described [30].

PKC Expression Increases the Levels of Soluble Vimentin in NPC1 Cells

NPC1 cells with missense or null (NPC1o) mutations contain decreased or virtually undetectable levels of soluble phosphorylated vimentin relative to WT cells, respectively [5]. Furthermore, the vimentin present in NPC1 cells exists as large disorganized filaments (dephosphorylated state) near the plasma membrane. Thus, NPC1 cells behave essentially as vimentin-null cells, which, similar to NPC1 cells, are unable to esterify LDL-derived cholesterol [11]. In extending those studies, it was hypothesized that decreased vimentin phosphorylation was the result of protein kinase C (PKC) inhibition in NPC1 cells. In support of this, it was observed in that study that treatment of NPC cells with the PKC activator phorbol-12-myristate-13-acetate (PMA) increased levels of soluble vimentin and ameliorated the NPC lipid storage phenotype, whereas conversely, treatment of WT cells with PKC inhibitors resulted in the disappearance of soluble vimentin in those cells. These results strongly implicate PKC in the maintenance of the soluble vimentin pool in cells and by extension normal lysosomal cholesterol efflux. Extending those studies by evaluating different PKC isoforms and their effects on soluble vimentin levels in NPC cells, it can be shown that the PKC isoforms a, βII, and ∊ have been implicated in vimentin phosphorylation [10, 17, 18]; therefore, the focus on these isoforms. They were transiently expressed in human NPC1 cells and their effects on soluble vimentin levels were characterized. Expression of PKC βII caused a significant increase in soluble vimentin levels (~38-fold higher than untransfected NPC1 cells), which was higher than the levels seen in WT cells (~20-fold higher than NPC1 cells), whereas expression of PKCs a or c caused smaller but still significant increases (~3-fold and ~7-fold, respectively) in soluble vimentin levels (FIG. 1). As a control, expression of Rab9 in these cells also led to a significant increase (~30-fold) in soluble vimentin, consistent with what was previously reported [5]. As noted all three isoforms resulted in an increase of soluble Rab9 levels to a similar degree (~2500-fold higher than untransfected NPC1 cells). Furthermore, insoluble vimentin levels decreased as soluble vimentin levels increased in PKCexpressing cells, suggesting that the increase in soluble vimentin was due to solubilization (phosphorylation) of insoluble vimentin (FIG. 1 panel A).

Similarly, in the severely affected NPC1o cells, which normally have almost no detectable soluble vimentin, expression of any of the three PKC isoforms resulted in increased levels of soluble vimentin (FIG. 1 panel B). With respect to vimentin solubilization, all three isoforms work equally well in the NPC1o cells, in contrast to the NPC1 cells, in which the βII isoform seemed to be the most effective in solubilizing vimentin. Furthermore, soluble Rab9 levels also increased to similar levels as a result of PKC expression (FIG. 1 panel B), a result also seen in PKC-expressing NPC1 cells (FIG. 1 panel A).

PKC Expression Induces Rab9 Dissociation from Vimentin

The observations that the small GTPase Rab9 is trapped in vimentin filaments in NPC1 cells [5] and that Rab9 overexpression corrects the NPC1 phenotype [19] strongly suggest that Rab9 availability is reduced in NPC1 cells. The disease cells may attempt to compensate for this deficit by upregulating Rab9 protein expression. This idea is supported by the fact that NPC1 cells do contain more Rab9 protein than WT cells (FIG. 1 panel A and [19]). As described above, PKC expression increased not only soluble vimentin levels but also soluble Rab9 levels significantly (FIG. 1). To determine whether the increased Rab9 levels in PKC-expressing cells was a result of Rab9 release from insoluble vimentin after it was phosphorylated, PKC assays were performed in vitro with nine purified PKC isoforms using the insoluble vimentin fraction of NPC1 cell lysates as the PKC substrate. All isoforms were able to effect Rab9 release from insoluble vimentin to varying degrees (FIG. 2), suggesting that, at least in vitro, most PKC isoforms can catalyze vimentin phosphorylation and Rab9 release. Interestingly, PKC α caused the greatest increase in Rab9 release, while PKC βII and ∊ were less effective and PKC γ was almost ineffective. These results differ from the results of transiently transfected PKC-expressing cells, which suggest that PKC βII is more effective in increasing soluble vimentin levels than PKC α and ∊ (FIG. 1 panel A). The discrepancies in isoform effectiveness may be due to the nature of the assays, the inherent activity of each isoform, or the in vivo subcellular location of the different isoforms and their access to vimentin [10, 16, 17, 20]; however, it is clear that PKC is able to solubilize vimentin and in doing so release entrapped Rab9.

Overexpression of PKCs Induces a Partial Correction of the NPC1 Phenotype

Figure 3:
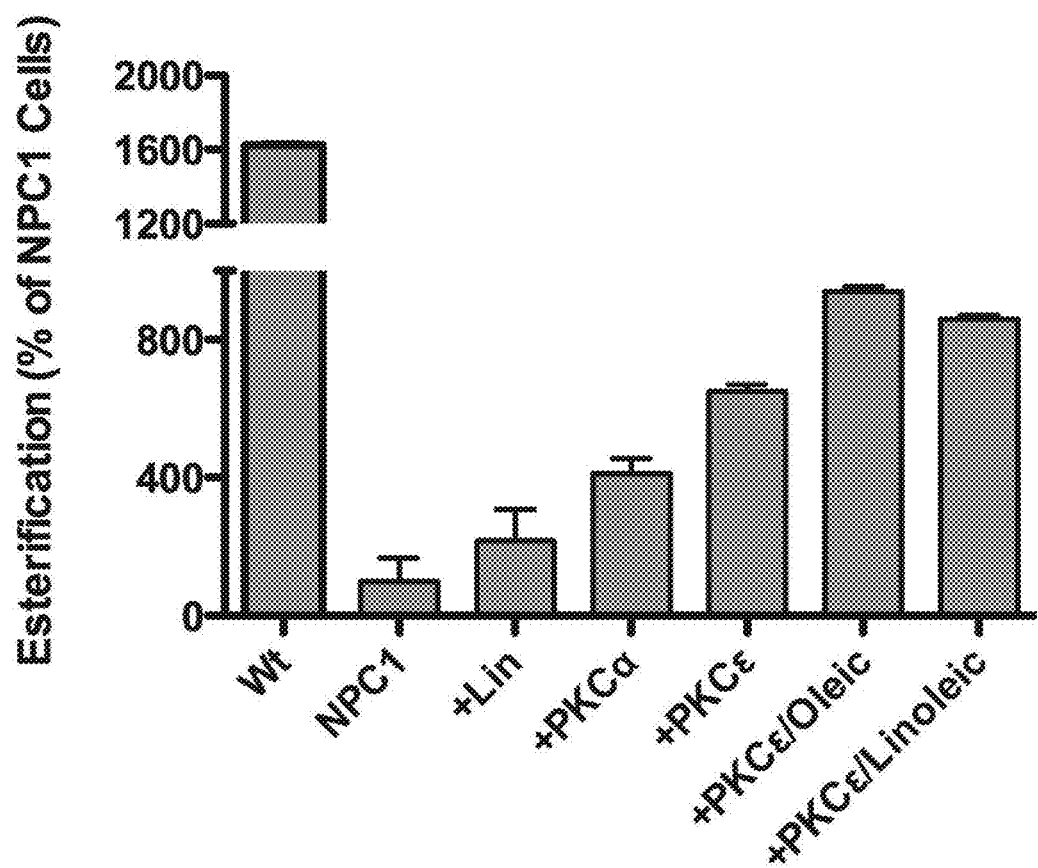

Based on the data above and observations that Rab9 overexpression results in increased soluble vimentin and correction of the NPC1 phenotype [5], it was determined whether increased vimentin solubility caused by PKC overexpression would also result in correction of the NPC1 phenotype. NPC1 CHO (M12) cells containing a deletion of the NPC1 locus [21] were transfected with PKC α or PKC ∊ and the amount of LDL-derived free cholesterol transported from the E/L system to the ER for esterification by acyl-CoA:cholesterol acyltransferase (ACAT) [22] was measured. Esterification levels for M12 cells were less than 10% of the esterification activity of the parental WT CHO cells (FIG. 3), which is consistent with a block in cholesterol transport out of the E/L system. Expression of PKC α or PKC ∊ ameliorated the cholesterol transport block, increasing the level of M12 cell esterification by approximately 4- and 6.5-fold, respectively, over that of untransfected M12 cells (FIG. 3, +PKCα, +PKCε). These results indicate that solubilization of vimentin mediated by expression of PKCs can partially release the NPC1 lipid transport block.

Figure 4:
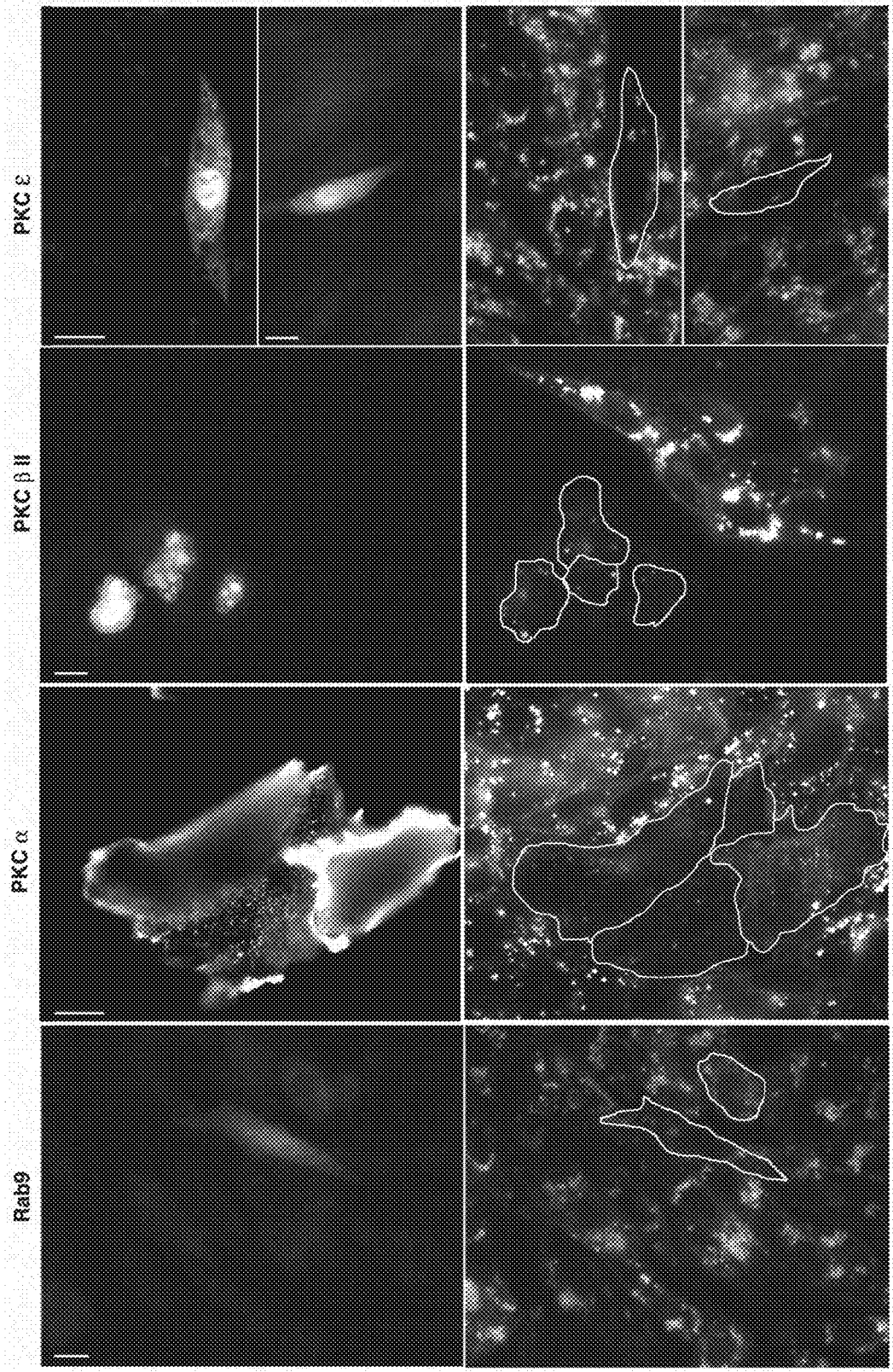

Cholesterol storage in PKC-transfected cells was also determined qualitatively by staining with filipin, a fluorescent probe that binds to free cholesterol [23]. This analysis yielded similar results to the esterification studies shown in FIG. 3. Cells that were positive (as determined by GFP co-expression) for PKCα, PKCε, or PKCβII showed significantly less filipin staining than surrounding untransfected cells (FIG. 4). These results were similar to those seen in cells over-expressing Rab9 (FIG. 4, Rab9), which has previously been shown to correct the NPC1 cholesterol storage phenotype [19].

Exposure to Fatty Acids Increases Soluble Vimentin Levels in NPC1 Cells

Fatty acids and in particular oleic acid have been shown to induce PKC activity [24], whereas a downstream metabolite of linoleic acid, DCP-LA (8-[2-(2-pentyl-cyclopropyl-methyl)-cyclopropyl]-octanoic acid), has been shown to potently activate PKC ε [25, 26]. Furthermore, it was shown previously that NPC1 endosomes store large amounts of fatty acids [27], which could potentially limit the amount of free fatty acids available to the cell for PKC activation and other processes.

To determine if exogenously added fatty acids can increase vimentin solubilization in NPC1 cells, human NPC1 fibroblasts were treated with oleic or linoleic acid for 48 hours and the levels of soluble vimentin in cell lysates were analyzed. NPC1 fibroblasts contain very little soluble vimentin (FIG. 5A and [5]). Treatment with either oleic or linoleic acid significantly increases the amount of soluble vimentin, with oleic acid being slightly more effective. These results suggest that exogenously added fatty acids can effect vimentin solubilization in NPC1 cells, presumably by activating PKCs.

Exposure to Fatty Acids Induces Correction of the NPC1 Phenotype

Since fatty acids increase solubilization of vimentin in NPC1 cells, they might also improve the NPC1 phenotype. M12 CHO cells (FIG. 5B) and human NPC1 fibroblasts (FIG. 5C) were treated with each fatty acid and then stained with filipin. WT cells (FIGS. 5B/C, 1) stain very weakly with filipin, whereas NPC1 (FIGS. 5B/C, 2) cells contain bright, punctate staining that is indicative of free cholesterol in endocytic vesicles. Filipin fluorescence in NPC1 cells from both species was significantly decreased after exposure to either fatty acid (FIGS. 5B/C, 3 and 4). Following quantitation of filipin fluorescence levels by integrated morphometry, both fatty acids were found to dramatically reduce the levels of cholesterol accumulation in both NPC1 cell lines, reducing filipin fluorescence to ~75% of levels in untreated cells (FIG. 5B/C, graphs). Human fibroblasts exhibit more heterogeneous filipin staining patterns than either CHO or mouse NPC1 cell lines, which is reflected in the higher standard deviation in untreated 3123 cells (FIG. 5C, graph). The effect of fatty acids on cholesterol esterification in M12 cells was also evaluated. Linoleic acid increased cholesterol esterification by greater than 2-fold compared to untreated M12 cells (FIG. 3, +Lin). In M12 cells treated with oleic or linoleic acids followed by expression of PKC ε, the correction of the NPC1 phenotype was more pronounced, with esterification levels that were ~3.5-fold over untreated cells (FIG. 3, +PKCε/oleic and +PKCε/linoleic). These results suggest that fatty acids and PKC expression have an additive effect on correction of the NPC1 cholesterol transport block.

To further characterize the effects of fatty acids on the NPC phenotype, the ability of docosahexanoic acid (DHA) and a metabolite of linoleic acid, DCP-LA, were tested for their ability to decrease cholesterol storage in M12 CHO cells. Both fatty acids have been shown to potently activate PKC ε [24, 28]. Treatment of M12 CHO cells with these compounds overnight resulted in decreased cholesterol storage (FIG. 6C/D) relative to untreated cells (FIG. 6B). DCP-LA (FIG. 6C) was slightly more effective than DHA (FIG. 6D). Quantitation of filipin intensity in these cells revealed that both compounds reduced cholesterol storage in M12 CHO cells by ~50% (FIG. 6G), lending further support to the positive effect of free fatty acids on the NPC disease phenotype, possibly through activation of PKC ε.

To provide further support for the role of PKCs in NPC rescue, M12 cells were treated with diazoxide, which has been shown to activate PKC ε [29]. This treatment resulted in reduced cholesterol accumulation in M12 CHO cells (FIG. 6F) relative to untreated cells (FIG. 6E). Quantitation of the filipin intensity in these cells indicated that diazoxide reduced cholesterol storage by ~50%, similar to the results seen with the free fatty acids (FIG. 6G).

Figure 7:
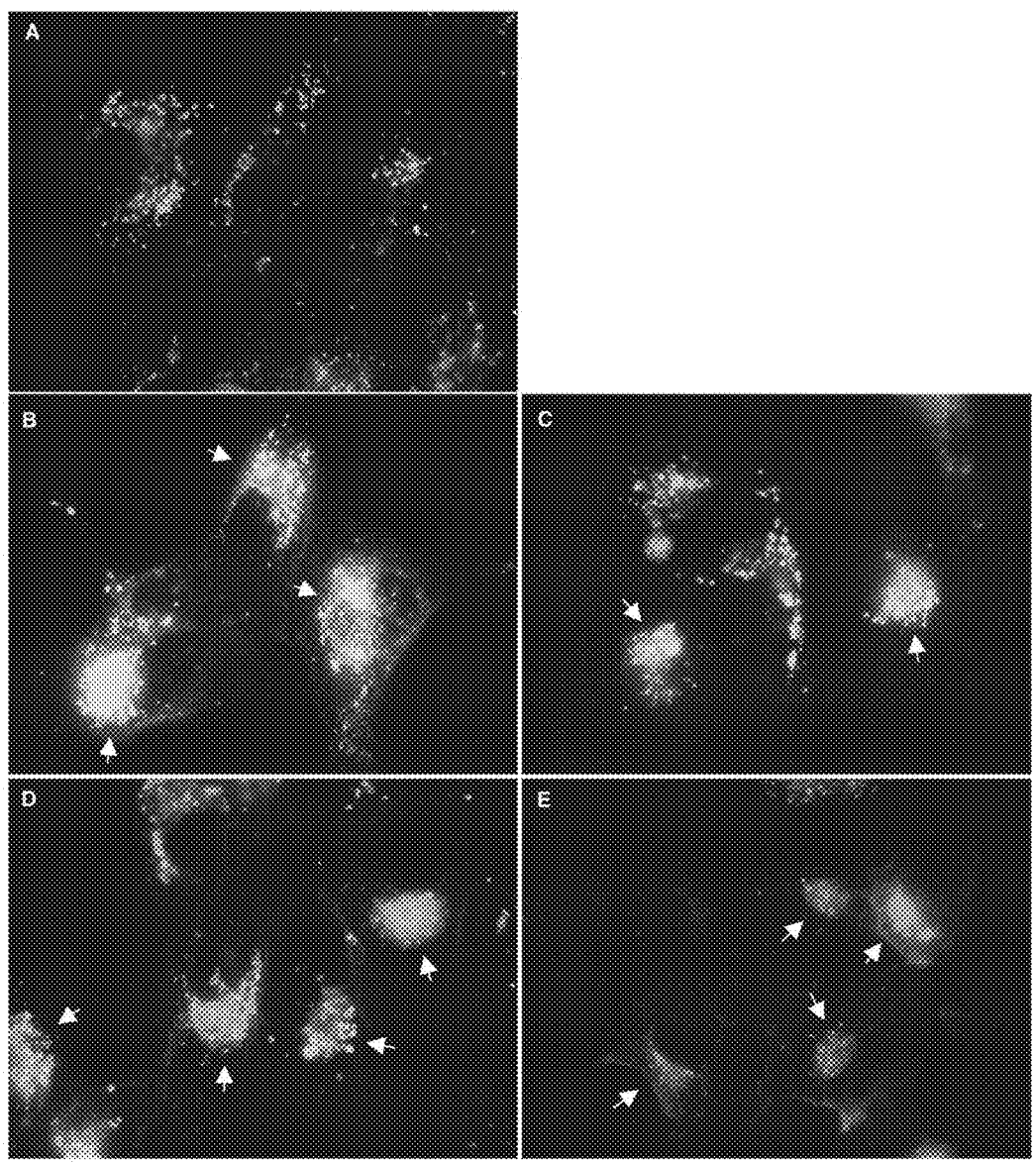

To further confirm the positive effects of DCP-LA and fatty acids on the NPC1 phenotype, human NPC1 cells were treated with DCP-LA, fatty acids, or PMA to activate PKCs. Cells were then labeled with BODIPY-LacCer, which has previously been shown to provide a dynamic view of the endocytic pathway [30]. Following absorption to the plasma membrane, the LacCer sphingolipid enters normal cells via endocytosis and eventually reaches the trans-Golgi network (TGN; [30]). Due to the lipid transport block in NPC1 cells however, this sphingolipid is trapped in endosomes and its targeting to the TGN is dramatically inhibited [30]. Human NPC1 cells treated as indicated in FIG. 7 show a dramatic improvement in lipid transport with the BODIPY-LacCer effectively reaching the TGN (FIG. 7; arrows) compared to untreated cells that show only punctate, endosomal fluorescence (FIG. 7A). These results provide further support that these agents are able to release the NPC1 lipid block.

Taken together, these results indicate that exposure to free fatty acids, which may act by activating PKCε, has a positive effect on the NPC cholesterol storage phenotype.

Discussion

Rab9 expression in NPC1 cells restored lipid transport from the E/L system and normalized cholesterol esterification [19] and subsequently showed that Rab9 was entrapped in insoluble vimentin filaments in NPC1 cells [5]. Consequently, accumulated lipids, such as sphingosine [31, 32] in NPC1 cells, might exert an inhibitory effect on various PKC isoforms, resulting in a disruption of the vimentin phosphorylation/dephosphorylation cycle [19].

To characterize the nature of PKC inhibition and vimentin hyposphorylation in NPC1 cells, a number of PKC isoforms (α, βII and ε) in NPC1 cells were expressed and their effect characterized on vimentin solubilization and correction of the NPC1 phenotype. All three isoforms had a positive effect on vimentin solubilization to varying degrees (FIG. 1).

Furthermore, PKC-induced vimentin solubilization was accompanied by the release of the entrapped Rab9 (FIG. 1). To further determine which PKC isoforms might be more effective in vimentin phosphorylation and release of Rab9, eight different PKC isoforms were tested in an in vitro assay. Most isoforms were able to release Rab9 from vimentin to varying degrees (FIG. 2), which may not be in case in vivo. This discrepancy is likely due to the different in vivo subcellular locations of PKC isoforms and their access to vimentin filaments [16, 20]. However, it is also possible that vimentin may not be a direct substrate for certain PKCs, as has been shown with regards to PKC ε-controlled phosphorylation of vimentin [10]. In that study, PKC c mediated vimentin phosphorylation, which was shown to be critical for proper integrin recycling through the cell. These studies indicate that expression of PKC isoforms in NPC1 cells results in the partial correction of the NPC1 disease phenotype, i.e., cholesterol accumulation in the endosomal/lysosomal system.

Figure 6:
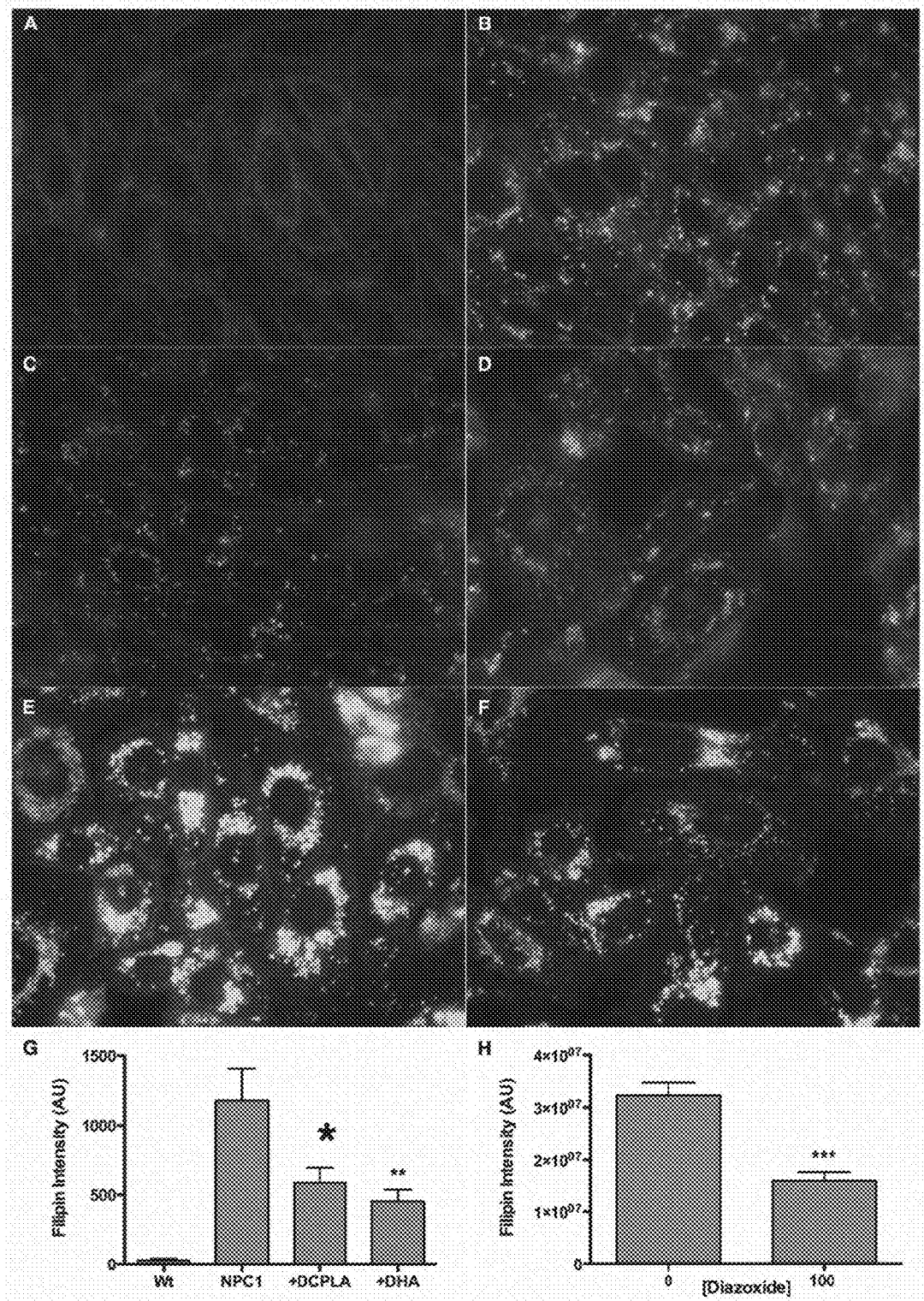

Also, many studies have shown that long chain fatty acids such asoleic and linoleic, along with downstream metabolites such as DCP-LA, are able to activate PKC ε [24, 25], an isoform shown to phosphorylate vimentin filaments [10]. Since it has been previously reported that the availability of free fatty acids may be limited in NPC1 cells [27, 33], exogenously added fatty acids were considered to have a positive effect on the NPC1 phenotype, presumably by activating PKC ε and leading to phosphorylation of vimentin and release of Rab9. As predicted, addition of oleic acid, linoleic acid, or DCP-LA resulted in an increase of soluble vimentin in NPC1 cells (FIG. 5). Furthermore, fatty acid addition resulted in a significant improvement in cholesterol esterification by NPC1 cells (FIG. 3), indicating that lipid transport from the E/L system was restored. The ability of diazoxide, a known activator of PKC ε [29], was tested to correct the NPC1 phenotype, providing further support for the involvement of insufficient PKC phosphorylation of vimentin in contributing to NPC1 pathogenesis. In agreement with the results presented here, diazoxide was able to reduce cholesterol accumulation in NPC1 cells by 50% (FIG. 6). Although results with multiple PKC ε activators strongly suggest that PKC ε is mediating these changes within the NPC cells, the possibility that these agents may be acting through some other pathway or protein besides PKC cannot be excluded.

These data are consistent with previous observations of aberrant PKC expression in NPC mouse liver [34]. In those studies the expression of PKC α, δ, ε, and ζ were evaluated by immunoblot. Whereas PKC α and δ were about 3-fold higher in NPC1 livers compared to WT livers, PKC ε was not significantly increased and PKC ζ was higher only in heterozygous livers. It is interesting to postulate that PKC ε does not render itself amenable to upregulation but can be activated, via fatty acids for example, and such activation can yield beneficial results in NPC1 cells. There is strong evidence that PKC ε is responsible for phosphorylating vimentin, which in turn controls the vesicular transport of various ligands such as integrins [10]. Considering the difficulties of delivering proteins as therapeutics, which are significantly amplified in diseases with neuropathology such as NPC1, a small lipid activator of a key regulator such as PKC ε would be greatly advantageous. These results suggest that identification of the PKC isoform(s) responsible for vimentin phosphorylation may provide new therapeutic targets for the treatment of Niemann-Pick type C disease, as well as other lysosomal storage disorders that lead to E/L lipid accumulation [35].

Example 2

We also studied the effect of the PKC activators bryostatin 1 and DCPLA on the phenotype of Niemann-Pick C disease using probes for free cholesterol (Filipin), glycosphingolipid levels (VTB) and gangliosides movement (CTB), following treatment of human NPC1 cells for 48-72 hrs.

Materials and Methods

TABLE 1

Human NPC1 Cell Lines

| | |
|---|---|
| NPC3---SV: | SV40 largeT immortalized |
| Species: | Human |
| Source: | Mount Sinai-Proprietary |
| NPC genotype: | V1165M and 3741-44delACTC |
| NPC24---SV: | SV40 largeT immortalized |
| Species: | Human |
| Source: | Mount Sinai-Proprietary |
| NPC genotype: | p.I1061T/p.I1061T |

TABLE 2

Reagents

| | |
|---|---|
| PKC Activators: | Bryostatin 1, DCPLA, Diazoxide |
| Source: | Santa Cruz Biotech, Sigma-Aldrich |
| Staining Reagents: | Filipin, Cholera toxin B, Verotoxin B |
| Source: | Polysciences, Sigma-Aldrich, MS Proprietary |

General Methodology

Cells are plated in 6-well dishes and treated with the appropriate compound (dissolved in DMSO) at the indicated dose daily for 48 hrs. Control cells receive DMSO. After 48 hrs cells are transferred to cover slips with fresh compound and grown for another 24 hrs. Cover slips are collected and processed for microscopy.

Assay Protocol

Filipin: For detection of unesterified cholesterol in lysosomes, cells were fixed in formalin for 30 min at 4° C., washed 2×, 5 min in 0.9% NaCl, incubated for 45 min with 0.01% filipin in PBS at room temperature, and then washed 2×, 5 min. Fluorescence was observed using a Nikon Eclipse fluorescence microscope (Nikon, Melville, N.Y.) equipped with a CCD camera. Fluorescence signals were quantified using Nikon's imaging and quantitation software package NIS *Elements*, v. 3.22.

Verotoxin B (VTB): For VTB staining (glycosphingolipid detection) cells are washed with PBS and fixed in formalin, 30 min, 4° C. Following a wash with 0.9% sodium chloride, 2×, 5 min at room temperature cells are permeabilized with digitonin 50 µg/well in 1.5 ml PBS. Cells are washed with PBS, and alexa-labeled VTB is added at 0.5 µg/well in 1 ml PBS. Cells are incubate 45 min at RT on a shaker in the dark, washed with 0.9% sodium chloride, 2×, 5 min at RT, and mounted for viewing.

Cholera toxin B (CTB): For CTB labeling (ganglioside movement) cells are washed with PBS, and 0.5 µg/well CTB is added in 1.5 ml Opti-MEM per well. Cells are incubated in a 37° C. incubator for 1 hr. Complete DMEM with FBS media is added and incubation is continued for 4 hr at 37° C. Cells are washed with PBS and fixed with formalin for 15 min at 4° C. Cells are washed with 0.9% sodium chloride, 2×, 5 min at RT and mounted for viewing.

Analysis, Results and Conclusions

Figure 2:
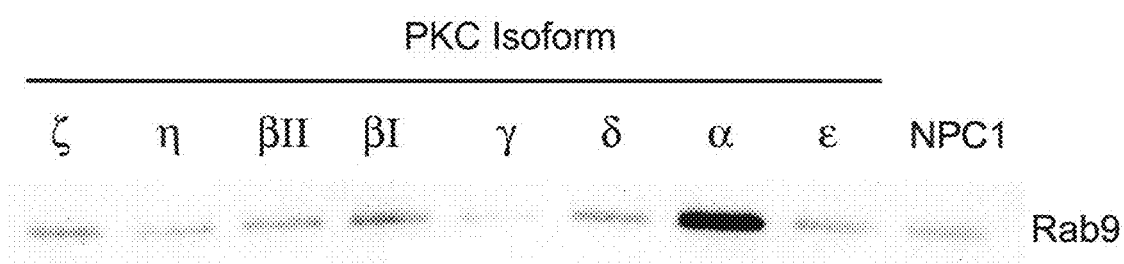

Niemann-Pick C1 (NPC1) cells have a defective NPC1 protein and are characterized by the extreme accumulation of a number of lipids such as cholesterol, sphingolipids and gangliosides in various endosomal vesicles (FIG. 2). In the characterization of NPC1 cells from various patients and evaluation of potential compounds that may be beneficial in treating this disease a number of different assays that measure the clearance and/or movement of various NPC1-specific lipids were performed. For example filipin was used to detect the level of stored cholesterol (Assay protocol) whereas verotoxin B (VTB) allows the assessment of the levels of glycosphingolipids which are sometimes stored in endosomes distinct from those that contain cholesterol (Assay protocol). In addition, movement of gangliosides from the plasma membrane by using a different probe, cholera toxin can be monitored (Assay protocol).

Figure 8:
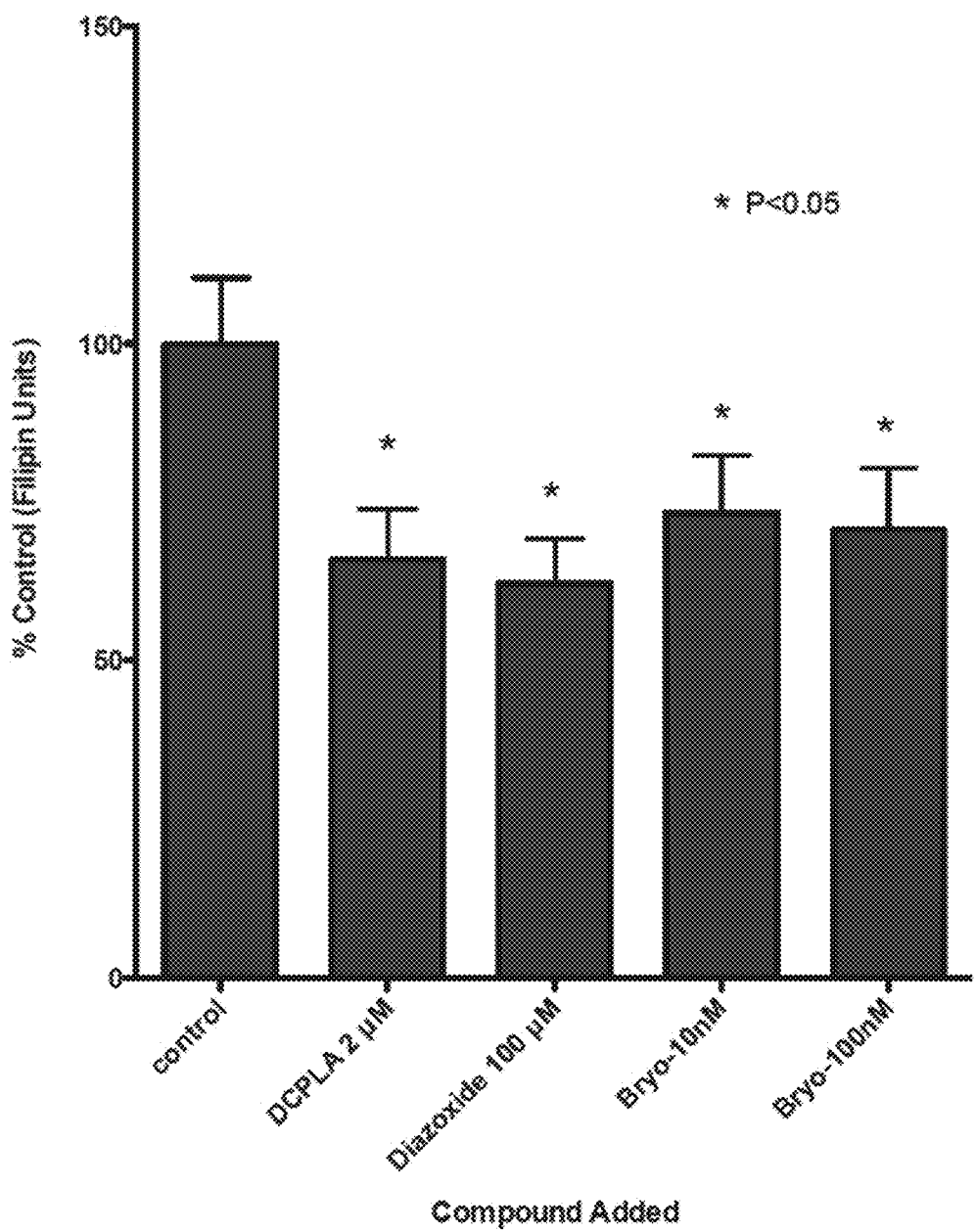
FIG. 8 is a graph showing the ability of DCPLA, diazoxide and bryostatin 1 to decrease stored cholesterol levels in NPC3-SV cells at 48 h.
Figure 9:
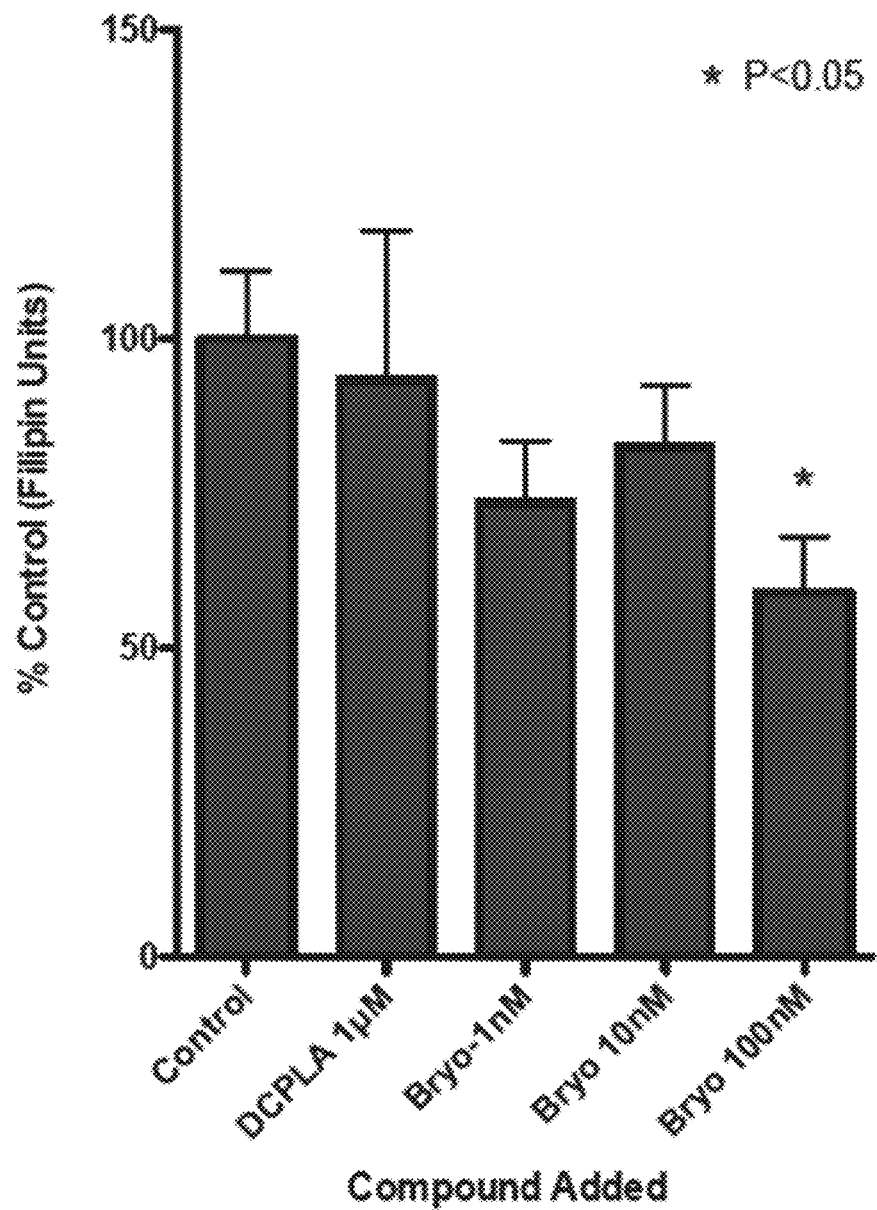
FIG. 9 is a graph showing the ability of DCPLA, and bryostatin 1 to decrease stored cholesterol levels in NPC3-SV cells at 72 h.
Figure 10:
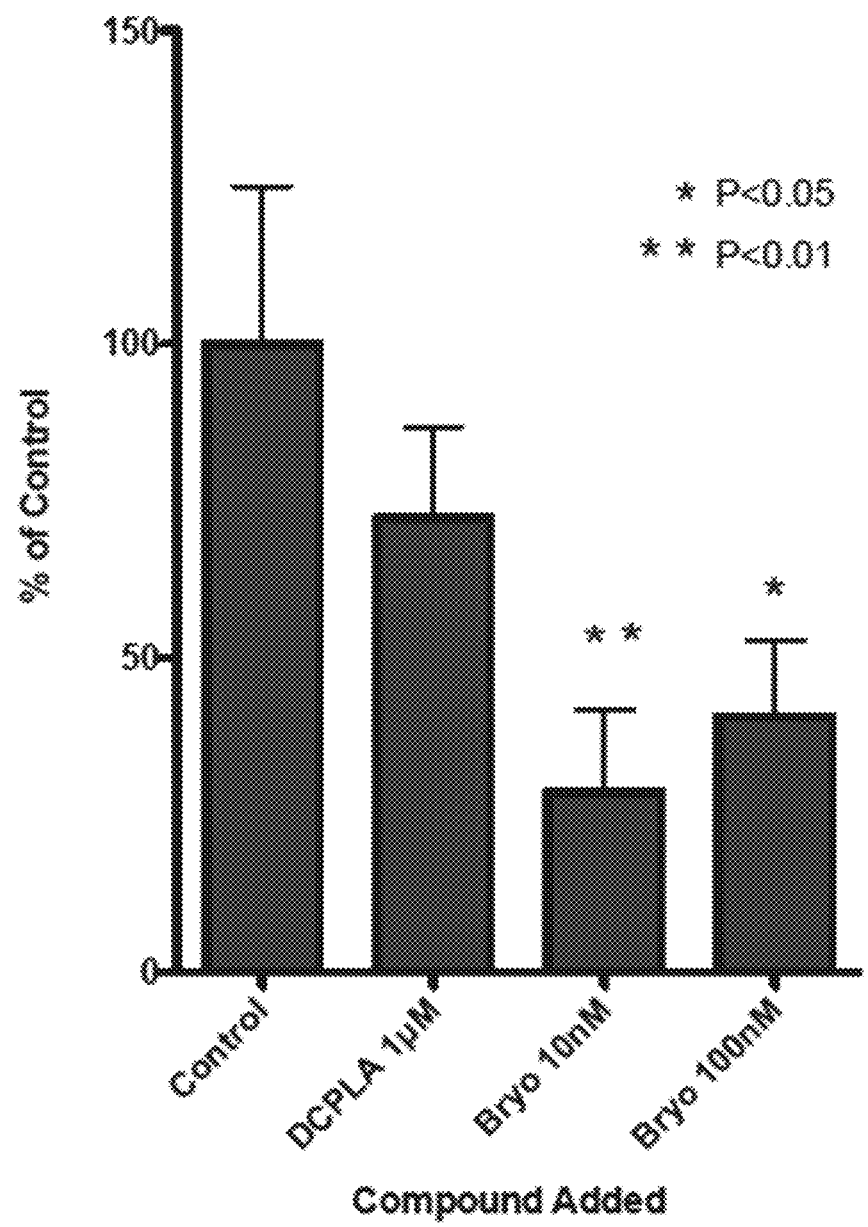
FIG. 10 is a graph showing the ability of DCPLA, and bryostatin 1 to decrease stored glycosphingolipid levels in NPC3-SV cells at 72 h using verotoxin B (VTB) as a probe stain.

These studies indicate that all three PKC activators, bryostatin 1, DCPLA and diazoxide are able to induce clearance of cholesterol from NPC1 cells to varying degrees and at different drug concentrations (FIG. 8). However, bryostatin 1 appears to be the most active compound showing activity in the nanomolar concentration range (FIG. 9). At 10 nM bryostatin 1 also shows statistically significant effectiveness in decreasing the glycosphingolipid accumulation of NPC1 cells (FIG. 10).

Figure 11:
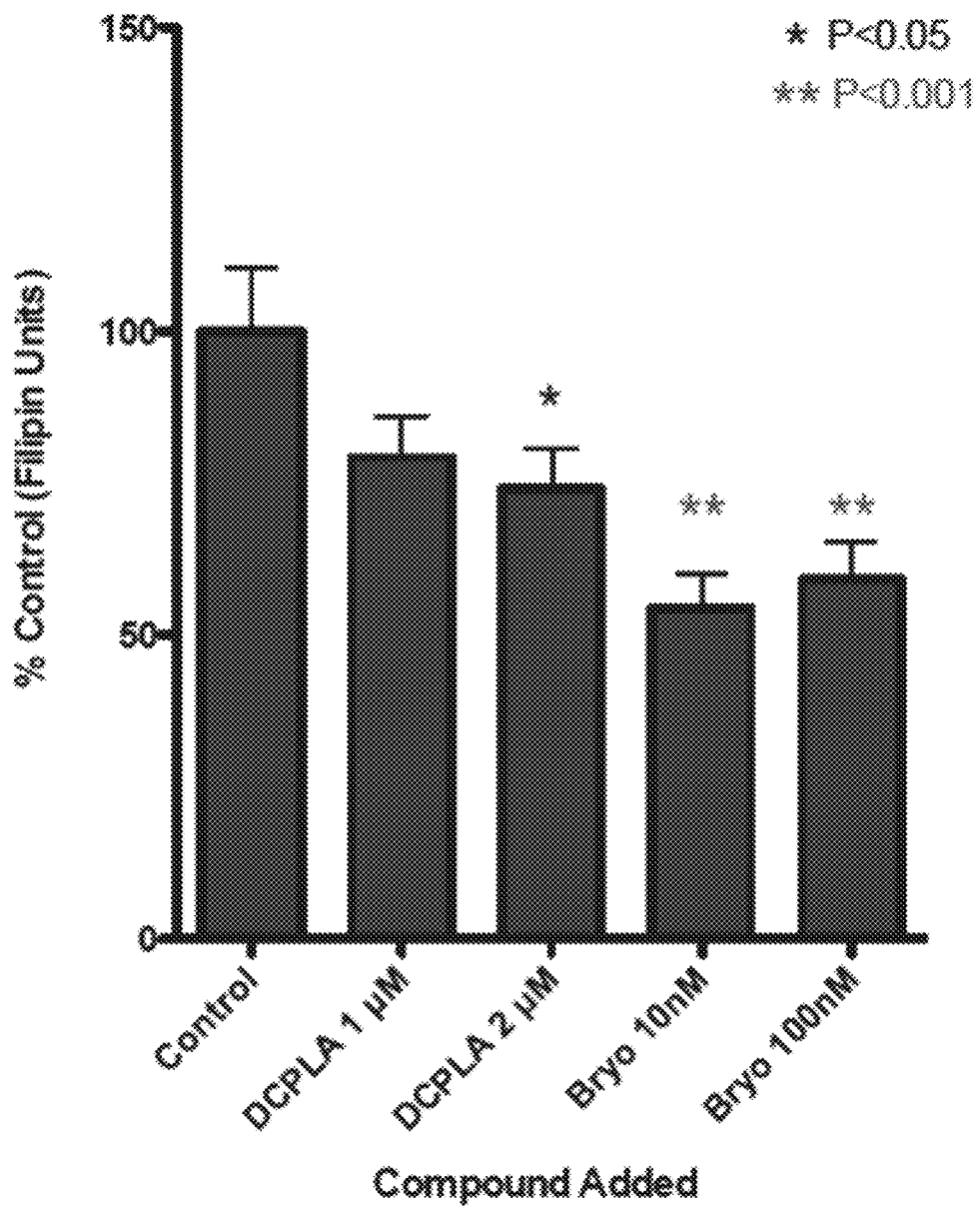
FIG. 11 is a graph showing the ability of DCPLA and bryostatin 1 to decrease filipin accumulation using an NPC24-SV cell line.

To determine whether the effects of bryostatin 1 is dependent on the genotype of the NPC1 cells used in the above experiments (i.e. the specific NPC1 gene mutations carried by a particular patient) a different patient cell line with a completely distinct NPC1 genotype was used. Bryostatin 1 was still able to effect cholesterol clearance from these cells at 10 nM concentration indicating that the activity of bryostatin 1 is independent of the NPC1 genotype (FIG. 11).

Figure 12:
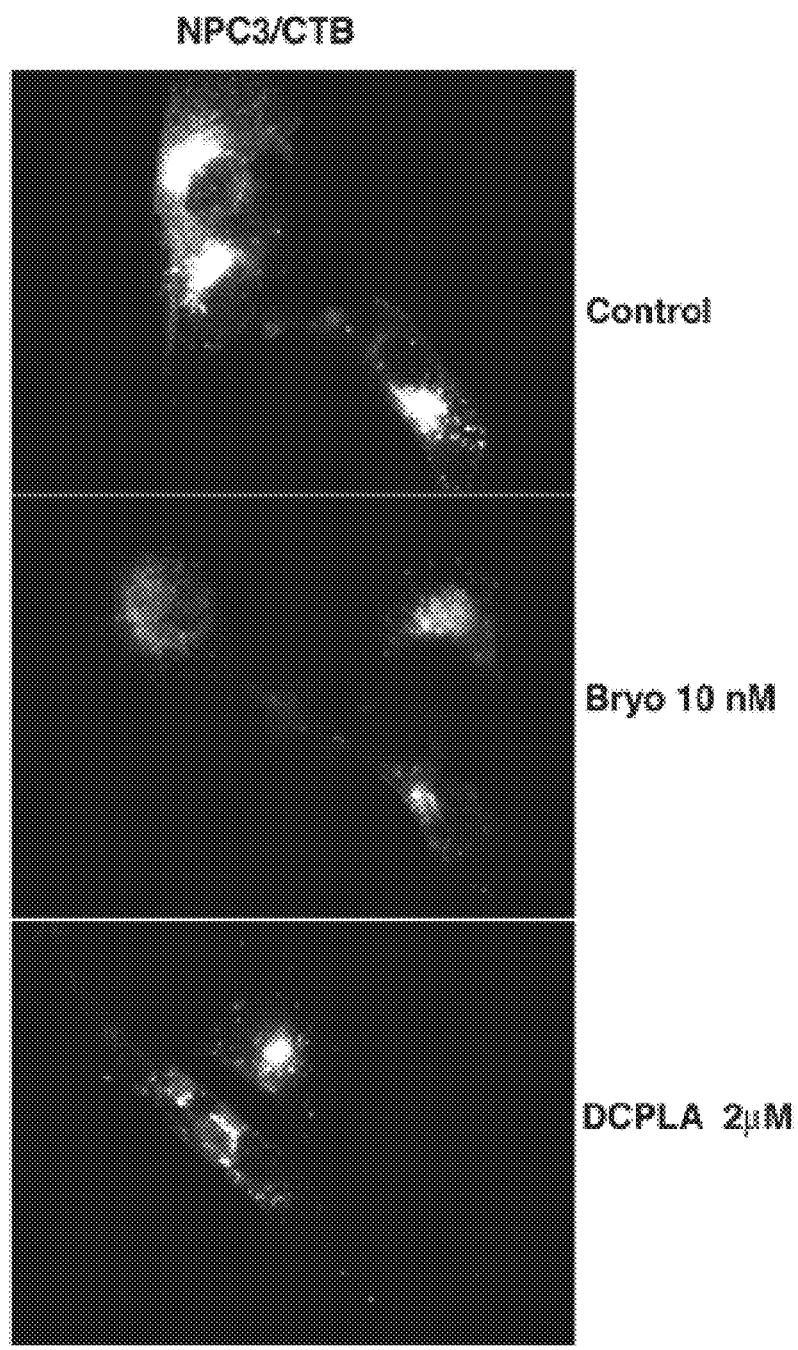
FIG. 12 are photomicrographs showing the ability of DCPLA, and bryostatin 1 to release the ganglioside transport block in NPC3SV cells.

Bryostatin 1 also was effective in a kinetic assay that monitors the movement of lipids from the plasma membrane to the Golgi network through endosomes. At 10 mM bryostatin 1 was able to clear the endosome-trapped cholera toxin (CTB) from NPC1 cells (FIG. 12).

Figure 13:
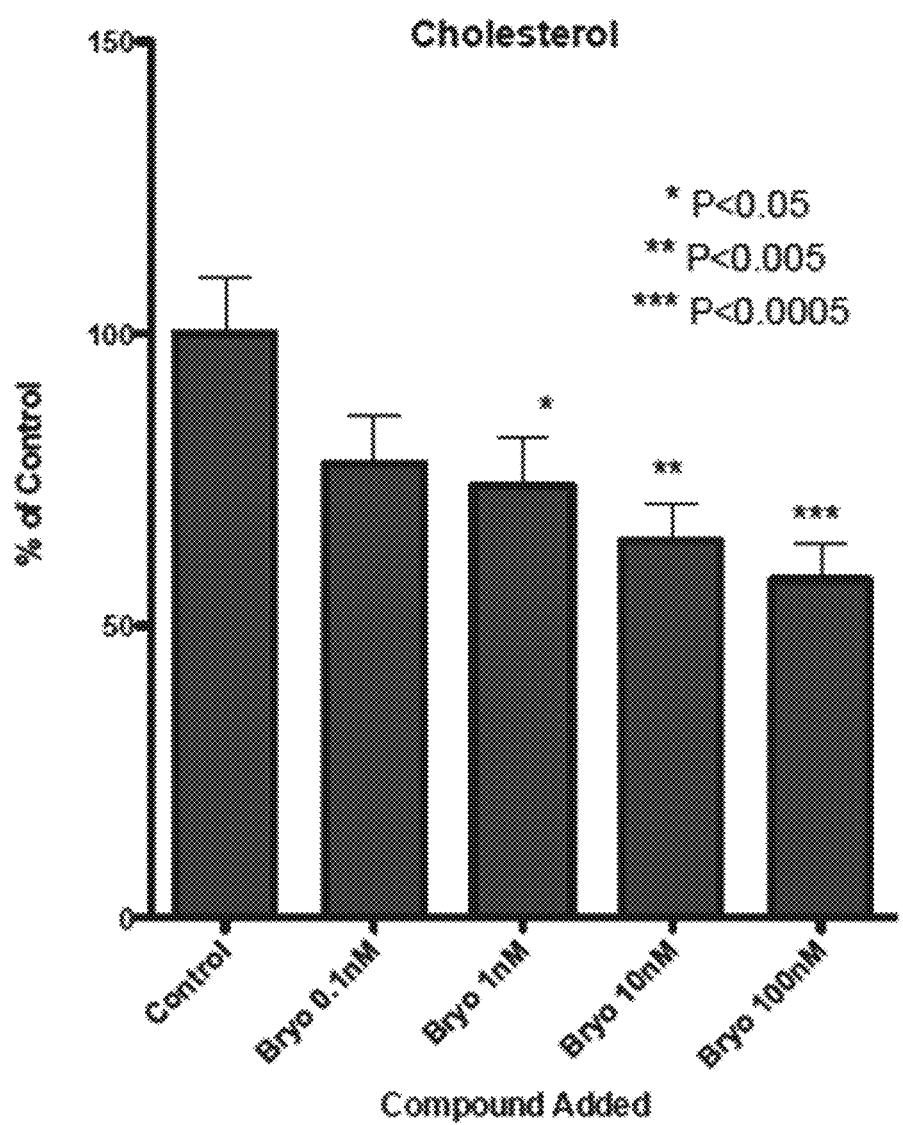
FIG. 13 is a graph showing the ability of bryostatin 1 (0.1-100 nM) to decrease cholesterol accumulation in human NPC24-SV cells.
Figure 14:
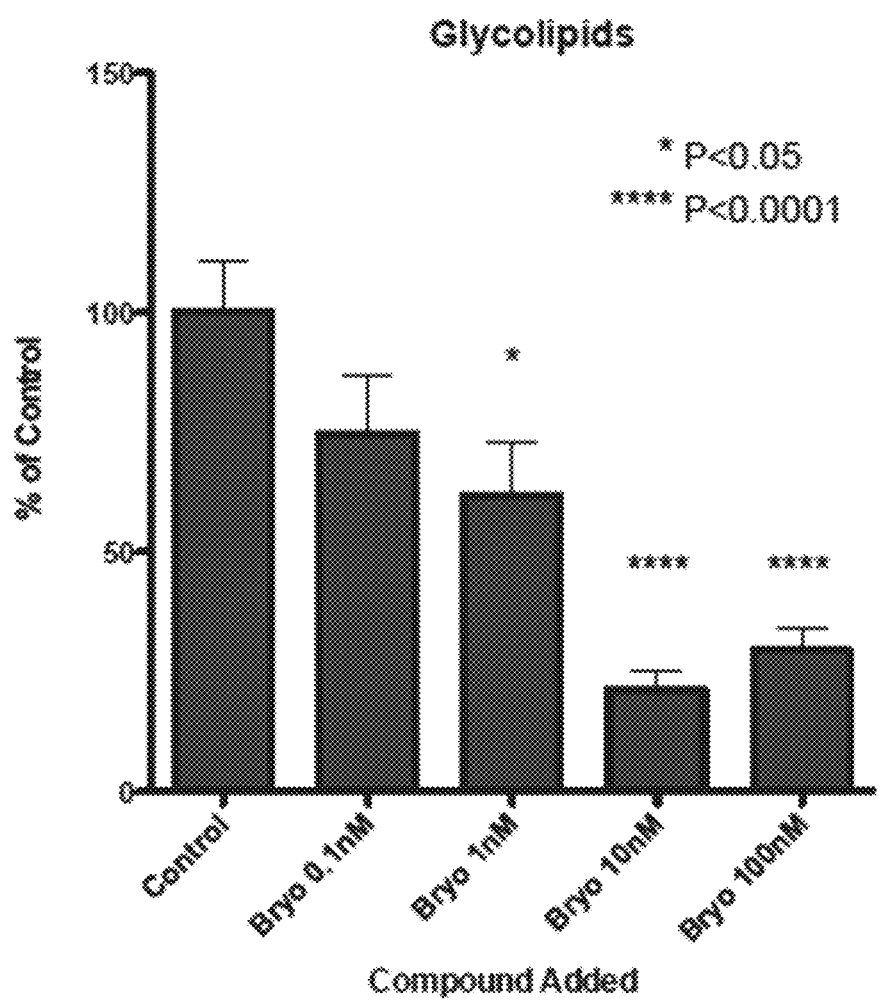
FIG. 14 is a graph showing the ability of bryostatin 1 (0.1-100 nM) to decrease glycosphingolipid accumulation in human NPC24-SV cells.
Figure 15:
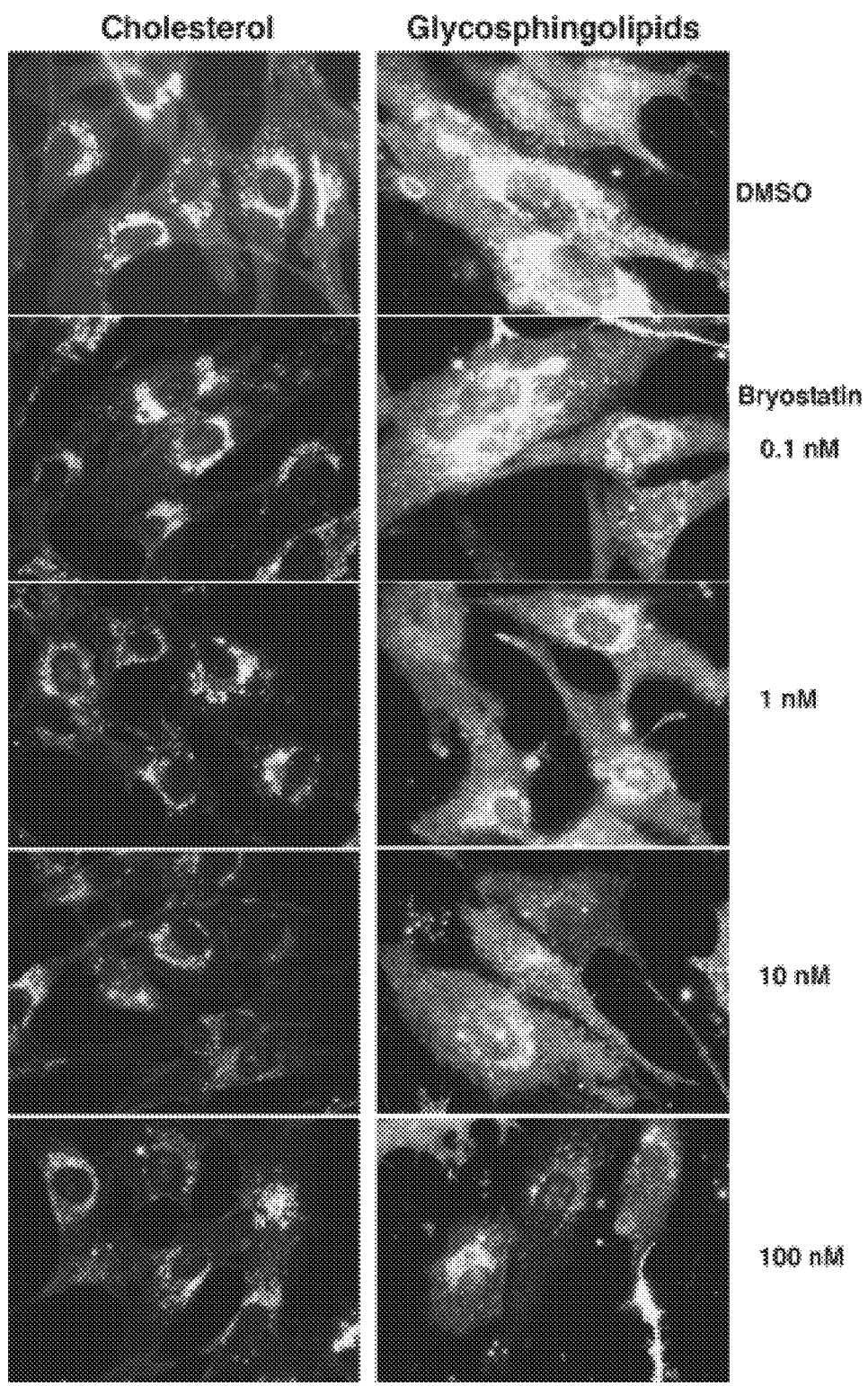
FIG. 15 are images showing representative fields of treated cells used in the analysis shown FIGS. 13-14.
Figure 16:
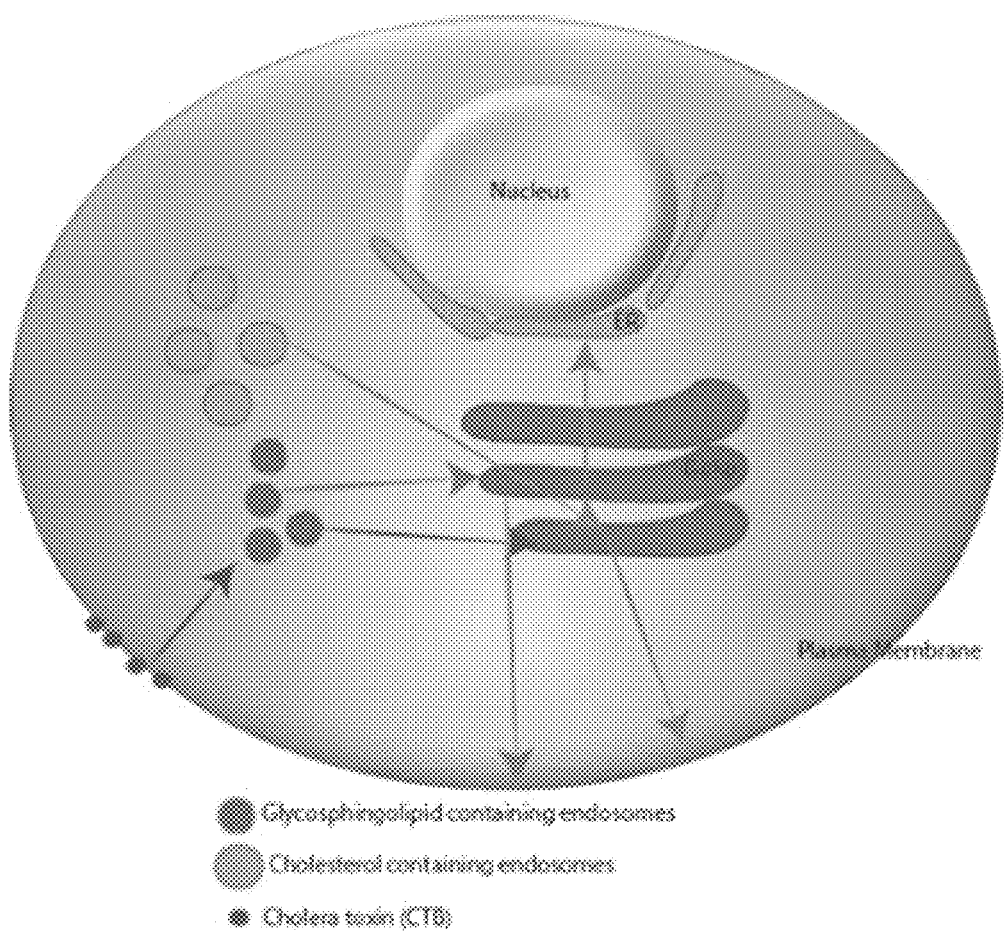
FIG. 16 is a graphic representation of an NPC1 cell showing the itineraries of various lipids stored.

To confirm these results bryostatin 1 was used at a range of 0.1 nM to 100 nM and evaluated both in cholesterol and sphingolipid assays (FIG. 13). At 0.1 nM bryostatin has no effect in both assays. The effect becomes statistically significant at 1 nM and increases with increasing bryostatin 1 concentration.

Accordingly, bryostatin 1 showed a positive therapeutic effect for human NPC1 disease cells at a concentration of 10-100 nM.

Example 3

Niemann-Pick C disease is a severe inherited lipidosis that leads to neurodegeneration and early childhood death. The biochemical and cellular events that lead to neurodegeneration are currently poorly understood. However, it has been shown that PKCε activation can restore the blocked lipid transport pathway and lead to a reduction of stored lipid material in the NPC endosomes/lysosomes. Thus, treatment of NPC1 mice with bryostatin 1, a natural product activator of PKCε, should lead to an improvement of disease progression in this animal model.

A total of 30 C57Bl6 NPC1 mice, mixed sex, were used. These mice were separated into 5 groups of 5 mice each, Groups 1-5.

Study Drug

Bryostatin 1 (purity≥95%) from Aphios (Woburn, Mass.), 1 vial 2 mg, was solubilized in a 5% DMSO, 20% Solutol and 75% Saline solution and used as the study drug. The negative (vehicle) control is a 5% DMSO, 20% Solutol and 75% Saline solution. DCP-LA from Sigma-Aldrich: 5 mg oil/vial was used as an additional in vitro active compound. Bryostatin 1 (API) was stored at or below −20° C. and formulated as needed. The formulated bryostatin 1 was stored at 2° to 8° C. for less than 24 hour(s). The DCP-LA and the vehicle controls were stored at 2°-8° C.

The stock solution of bryostatin 1 is 10 mg/ml in DMSO, which is kept at −80° C. in aliquots. The dosing formulation is made by diluting the stock first in DMSO, then adding solutol, and lastly saline—with more insoluble compounds, adding the drug stock to complete vehicle will cause the compound to come out of solution, so we make formulations stepwise. The dosing volume is always 100 μl. Mice weigh approximately 20 g.

Dosing and Frequency

The study agents are dosed intraperitoneally (IP) as shown in Table 3. The mice are dosed twice weekly (Mon and Thu) starting at 30 days for up to 150 days.

TABLE 3

Dosing regimen

| Group | Agent | Dosing |
|---|---|---|
| Group 1: | Vehicle control (mL) | |
| Group 2: | Bryostatin-1 | [BHD-1] 40 μg/kg (120 μg/m$^2$) |
| Group 3: | Bryostatin-1 | [BHD-2] 30 μg/kg (90 μg/m$^2$) |
| Group 4: | Bryostatin-1 | [BHD-3] 20 μg/kg (60 μg/m$^2$) |
| Group 5: | Bryostatin-1 | [BHD-4] 10 μg/kg (30 μg/m$^2$) |
| Group 6: | Bryostatin-1 | [BHD-5] 5 μg/kg (15 μg/m$^2$) |
| Group 7 | Active | (DCP-LA 3 mg oil/kg) |

Study Duration

Figure 17:
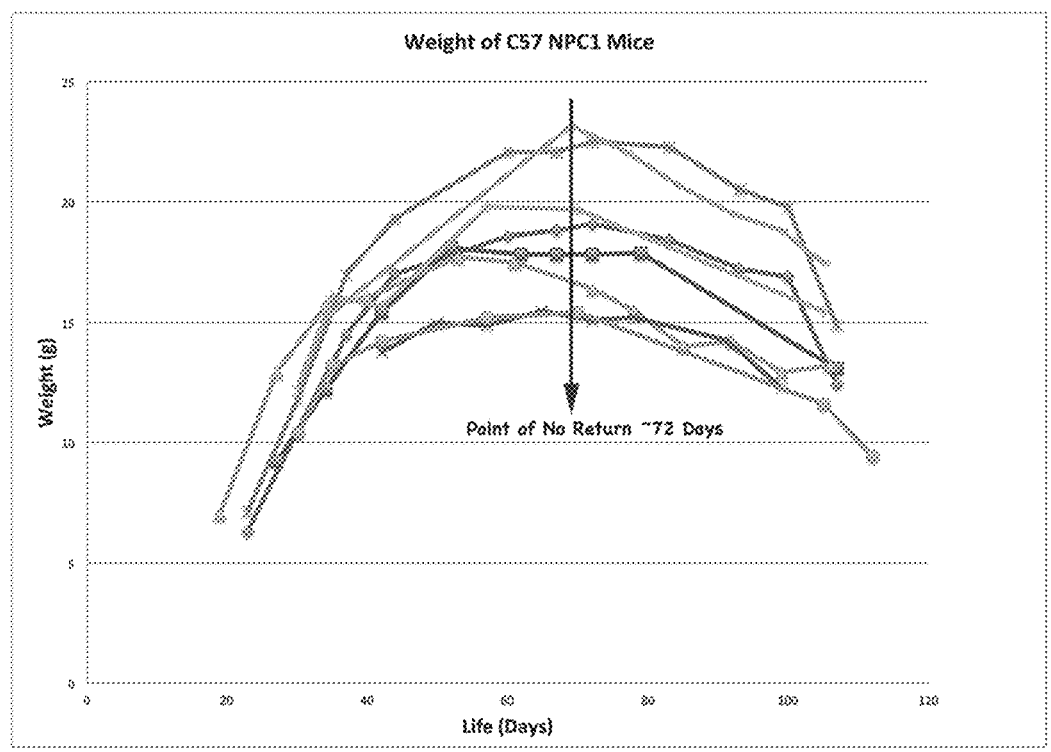
FIG. 17 is a graph showing untreated C57 NPC1 mice. Weight gain is observed up to around day 70-72 of life after which a rapid weight loss is observed.

C57 NPC1 mice have an average life span of ~110 days. By Day 70 mice reach an average weight of 18-22 grams. Untreated NPC1 mice develop ataxia and will begin to lose weight at ~70 days (see FIG. 17). Ataxia (or lack of voluntary muscle control) is a clinical feature of NPC1 mice, which may be described as shaking. Treatment will be initiated at ~30 days of age, average NPC mouse weight of 10 g. If the drug is efficacious injections will continue past day 70-80. An extension of life of about 20-30% will mean that animals will need to be treated up to day 130-150.

Data Collection

Initially mice will be weighed and weights will be recorded prior to each injection. Mice may periodically be tested in a rotarod and time on rotarod will be recorded.

Upon euthanasia blood will be collected and the brains will be frozen and stored for evaluation of cholesterol storage and Purkinje cell survival. In addition, the livers and spleens from these mice will be extracted, prepared for histology and stored frozen for the option of determining the effects of bryostatin 1 treatment on peripheral organ lipid accumulation.

Data Analysis

Primary outcome will be weights collected on dosing days (2×/week) over the course of the study. Differences will be examined between vehicle control and different doses of bryostatin 1, particularly after age 70 days, when animals have historically experienced a weight loss.

Secondary outcomes include: (1) lipid accumulation in liver and spleen, and (2) cerebellar Purkinje cell survival and cholesterol storage (which are to be conducted only if the primary outcome is positive).

Results

Mice in dose groups 30, 20 and 10 μg/kg lived past the age of 100 days.

One of skill in the art will appreciate that the examples herein are not intended to be limiting and that one of skill in the art will readily be able to apply the teachings herein to treating lipid storage disorders. Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

REFERENCES

1. Mellor H, Parker P J (1998) The extended protein kinase C superfamily. Biochem J 332(2): 281-292. PubMed: 9601053.
2. Azzi A, Boscoboinik D, Hensey C (1992) The protein kinase C family. Eur J Biochem 208: 547-557. doi: 10.1111/j.1432-1033.1992.tb17219.x. PubMed: 1396661.
3. Cloud-Heflin B A, McMasters R A, Osborn M T, Chambers T C (1996) Expression, subcellular distribution and response to phorbol esters of protein kinase C (PKC) isozymes in drug-sensitive and multidrugresistant KB cells evidence for altered regulation of PKC-alpha. Eur J Biochem 239: 796-804. doi:10.1111/j.1432-1033.1996.0796u.x. PubMed: 8774728.
4. Mochly-Rosen D, Das K, Grimes K V (2012) Protein kinase C, an elusive therapeutic target? Nat Rev Drug Discov 11: 937-957. doi: 10.1038/nrd3871. PubMed: 23197040.
5. Walter M, Chen F W, Tamari F, Wang R, Ioannou Y A (2009) Endosomal lipid accumulation in NPC1 leads to inhibition of PKC, hypophosphorylation of vimentin and Rab9 entrapment. Biol Cell 101: 141-152. doi:10.1042/BC20070171. PubMed: 18681838.
6. Shen W J, Zaidi S K, Patel S, Cortez Y, Ueno M et al. (2012) Ablation of vimentin results in defective steroidogenesis. Endocrinology 153: 3249-3257. doi:10.1210/en.2012-1048. PubMed: 22535769.
7. Styers M L, Kowalczyk A P, Faundez V (2005) Intermediate filaments and vesicular membrane traffic: the odd couple's first dance? Traffic 6: 359-365. doi:10.1111/j.1600-0854.2005.00286.x. PubMed: 15813746.
8. Perlson E, Hanz S, Ben-Yaakov K, Segal-Ruder Y, Seger R et al. (2005) Vimentin-dependent spatial translocation of an activated MAP kinase in injured nerve. Neuron 45: 715-726. doi:10.1016/j.neuron. 2005.01.023. PubMed: 15748847.
9. Toda M, Kuo C H, Borman S K, Richardson R M, Inoko A et al. (2012) Evidence that formation of vimentin mitogen-activated protein kinase (MAPK) complex mediates mast cell activation following FcepsilonRI/CC chemokine receptor 1 cross-talk. J Biol Chem 287: 24516-24524. doi:10.1074/jbc.M111.319624. PubMed: 22613718.
10. Ivaska J, Vuoriluoto K, Huovinen T, Izawa I, Inagaki M et al. (2005) PKCepsilon-mediated phosphorylation of vimentin controls integrin recycling and motility. EMBO J 24: 3834-3845. doi:10.1038/sj.emboj. 7600847. PubMed: 16270034.
11. Sarria A J, Panini S R, Evans R M (1992) A functional role for vimentin intermediate filaments in the metabolism of lipoprotein-derived cholesterol in human SW-13 cells. J Biol Chem 267: 19455-19463. PubMed: 1527066.
12. Eriksson J E, He T, Trejo-Skalli A V, Härmälä-Brasken A S, Hellman J et al. (2004) Specific in vivo phosphorylation sites determine the assembly dynamics of vimentin intermediate filaments. J Cell Sci 117: 919-932. doi: 10.1242/jcs.00906. PubMed: 14762106.
13. Klymkowsky M W (1995) Intermediate filament organization, reorganization, and function in the clawed frog Xenopus. Curr Top Dev Biol 31: 455-486. PubMed: 8746673.
14. Mor-Vaknin N, Punturieri A, Sitwala K, Markovitz D M (2003) Vimentin is secreted by activated macrophages. Nat Cell Biol 5: 59-63. PubMed: 12483219.
15. Mangoura D, Sogos V, Dawson G (1995) Phorbol esters and PKC signaling regulate proliferation, vimentin cytoskeleton assembly and glutamine synthetase activity of chick embryo cerebrum astrocytes in culture. Brain Res Dev Brain Res 87: 1-11. doi: 10.1016/0165-3806(95)00046-G. PubMed: 7554227.
16. Spudich A, Meyer T, Stryer L (1992) Association of the beta isoform of protein kinase C with vimentin filaments. Cell Motil Cytoskeleton 22: 250-256. doi:10.1002/cm.970220405. PubMed: 1516148.
17. Szalay J, Bruno P, Bhati R, Adjodha J, Schueler D et al. (2001) Associations of PKC isoforms with the cytoskeleton of B16F10 melanoma cells. J Histochem Cytochem 49: 49-66. doi: 10.1177/002215540104900106. PubMed: 11118478.
18. Bertrand F, Veissiere D, Hermelin B, Paul A, Capeau J et al. (1994) Phosphorylation of vimentin is an intermediate step in protein kinase Cmediated glycoconjugate secretion. Am J Physiol 266: C611-C621. PubMed: 7513122.
19. Walter M, Davies J P, Ioannou Y A (2003) Telomerase immortalization upregulates Rab9 expression and restores LDL cholesterol egress from Niemann-Pick C1 late endosomes. J Lipid Res 44: 243-253. doi: 10.1194/jlr.M200230-MR200. PubMed: 12576506.
20. Disatnik M H, Buraggi G, Mochly-Rosen D (1994) Localization of protein kinase C isozymes in cardiac myocytes. Exp Cell Res 210: 287-297. doi:10.1006/excr.1994.1041. PubMed: 8299726.
21. Millard E E, Srivastava K, Traub L M, Schaffer J E, Ory D S (2000) Niemann-pick type C1 (NPC1) overexpression alters cellular cholesterol homeostasis. J Biol Chem 275: 38445-38451. doi:10.1074/jbc.M003180200. PubMed: 10964915.
22. Pentchev P G, Boothe A D, Kruth H S, Weintroub H, Stivers J et al. (1984) A genetic storage disorder in BALB/C mice with a metabolic block in esterification of exogenous cholesterol. J Biol Chem 259: 5784-5791. PubMed: 6325448.
23. Bolard J (1986) How do the polyene macrolide antibiotics affect the cellular membrane properties? Biochim Biophys Acta 864: 257-304. doi:10.1016/0304-4157(86)90002-X. PubMed: 3539192.
24. Khan W A, Blobe G, Halpern A, Taylor W, Wetsel W C et al. (1993) Selective regulation of protein kinase C isoenzymes by oleic acid in human platelets. J Biol Chem 268: 5063-5068. PubMed: 8444883.
25. Kanno T, Yamamoto H, Yaguchi T, Hi R, Mukasa T et al. (2006) The linoleic acid derivative DCP-LA selectively activates PKC-epsilon, possibly binding to the phosphatidylserine binding site. J Lipid Res 47:1146-1156. doi:10.1194/jlr.M500329-MR200. PubMed: 16520488.
26. Tanaka A, Nishizaki T (2003) The newly synthesized linoleic acid derivative FR236924 induces a long-lasting facilitation of hippocampal neurotransmission by targeting nicotinic acetylcholine receptors. Bioorg Med Chem Lett 13: 1037-1040. doi: 10.1016/S0960-894X(03)00089-1 PubMed: 12643906
27. Chen F W, Gordon R E, Ioannou Y A (2005) NPC1 late endosomes contain elevated levels of non-esterified ('free') fatty acids and an abnormally glycosylated form of the NPC2 protein. Biochem J 390: 549-561. doi: 10.1042/BJ20050236. PubMed: 15896196.
28. Nishizuka Y (1992) Intracellular signaling by hydrolysis of phospholipids and activation of protein kinase C. Science 258: 607-614. doi:10.1126/science. 1411571. PubMed: 1411571.

29. Kim M Y, Kim M J, Yoon I S, Ahn J H, Lee S H et al. (2006) Diazoxide acts more as a PKC-epsilon activator, and indirectly activates the mitochondrial K(ATP) channel conferring cardioprotection against hypoxic injury. Br J Pharmacol 149: 1059-1070. PubMed: 17043673.
30. Puri V, Watanabe R, Dominguez M, Sun X, Wheatley C L et al. (1999) Cholesterol modulates membrane traffic along the endocytic pathway in sphingolipid-storage diseases. Nat Cell Biol 1: 386-388. doi: 10.1038/14084. PubMed: 10559968.
31. Goldin E, Roff C F, Miller S P, Rodriguez-Lafrasse C, Vanier M T et al. (1992) Type C Niemann-Pick disease: a murine model of the lysosomal cholesterol lipidosis accumulates sphingosine and sphinganine in liver. Biochim Biophys Acta 1127: 303-311. doi: 10.1016/0005-2760 (92)90236-O. PubMed: 1324734.
32. Rodriguez-Lafrasse C, Rousson R, Valla S, Antignac P, Louisot P et al. (1997) Modulation of protein kinase C by endogenous sphingosine inhibition of phorbol dibutyrate binding in Niemann-Pick C fibroblasts. Biochem J 325 (3): 787-791. PubMed: 9271101.
33. Leventhal A R, Leslie C C, Tabas I (2004) Suppression of macrophage eicosanoid synthesis by atherogenic lipoproteins is profoundly affected by cholesterol-fatty acyl esterification and the Niemann-Pick C pathway of lipid trafficking J Biol Chem 279: 8084-8092. PubMed: 14638686.
34. Garver W S, Hossain G S, Winscott M M, Heidenreich R A (1999) The Npc1 mutation causes an altered expression of caveolin-1, annexin II and protein kinases and phosphorylation of caveolin-1 and annexin II in murine livers. Biochim Biophys Acta 1453: 193-206. doi: 10.1016/50925-4439(98)00101-X. PubMed: 10036317.
35. Ioannou Y A (2004) Defects in transmembrane proteins. In: SUW, F M Platt. Lysosomal disorders of the brain. New York: Oxford University Press. pp. 206-228.
36. Ioannou Y A, Zeidner K M, Gordon R E, Desnick R J (2001) Fabry disease: preclinical studies demonstrate the effectiveness of alphagalactosidase A replacement in enzyme-deficient mice. Am J HumGenet 68: 14-25. doi: 10.1086/316953. PubMed: 11115376.
37. Higgins M E, Davies J P, Chen F W, Ioannou Y A (1999) Niemann-Pick C1 is a late endosome-resident protein that transiently associates with lysosomes and the trans-Golgi network. Mol Genet Metab 68: 1-13. doi: 10.1006/mgme.1999.2882. PubMed: 10479477.

We claim:

1. A method comprising: administering to a subject with a lipid storage disorder a pharmaceutically effective amount of bryostatin 1.

2. A method comprising: administering to a subject with a lipid storage disorder a pharmaceutically effective amount of bryostatin 2-20, a bryolog, or combinations thereof.

3. The method of claim 1 wherein the lipid storage disorder is selected from Niemann-Pick disease, Gaucher disease, Fabry disease, a gangliosidoses, Tay-Sachs disease, Sandhoff disease, Krabbe disease, metachromatic leukodystrophy, Wolman's disease, and cholesteryl ester storage disease.

4. The method of claim 1 wherein the lipid storage disorder is Niemann-Pick Type C disease.

5. The method of claim 1 wherein the pharmaceutically effective amount of bryostatin 1 is from about 0.0000001 mg/kg to about 250 mg/kg per dose.

6. The method of claim 1 wherein the bryostatin 1 is administered from 1 to 4 times per day, twice a week, once a week, once every two weeks, once every three weeks, once every four weeks, once every six weeks, once every eight weeks; or less frequently.

7. The method of claim 1 wherein the bryostatin 1 the PKC activator is administered orally, intraperitoneally, subcutaneously, intranasally, intramuscularly, buccally, trans-dermally or intravenously.

8. The method of claim 1 wherein the pharmaceutically effective amount of bryostatin 1 is from about 0.00001 mg/kg to about 5.0 mg/kg per dose.

9. The method of claim 1 wherein the bryostatin 1 is administered at a dose from 0.01-25 µg/m$^2$ IV.

10. A method comprising: administering to a subject with Niemann-Pick Type C disease a pharmaceutically effective amount of bryostatin 1.

11. The method of claim 2 wherein the lipid storage disorder is selected from Niemann-Pick disease, Gaucher disease, Fabry disease, a gangliosidoses, Tay-Sachs disease, Sandhoff disease, Krabbe disease, metachromatic leukodystrophy, Wolman's disease, and cholesteryl ester storage disease.

12. The method of claim 2 wherein the lipid storage disorder is Niemann-Pick Type C disease.

13. The method of claim 2 wherein the pharmaceutically effective amount of bryostatin 2-20 or bryolog is from about 0.0000001 mg/kg to about 250 mg/kg per dose.

14. The method of claim 2 wherein the bryostatin 2-20 or bryolog is administered from 1 to 4 times per day, twice a week, once a week, once every two weeks, once every three weeks, once every four weeks, once every six weeks, once every eight weeks; or less frequently.

15. The method of claim 2 wherein the bryostatin 2-20 or bryolog is administered orally, intraperitoneally, subcutaneously, intranasally, intramuscularly, buccally, trans-dermally or intravenously.

16. The method of claim 2 wherein the pharmaceutically effective amount of bryostatin 2-20 or bryolog is from about 0.00001 mg/kg to about 5.0 mg/kg per dose.

17. The method of claim 2 wherein the bryostatin 2-20 or bryolog is administered at a dose from 0.01-25 µg/m$^2$ IV.

18. The method of claim 10 wherein the pharmaceutically effective amount of bryostatin 1 is from about 0.0000001 mg/kg to about 250 mg/kg per dose.

19. The method of claim 10 wherein the pharmaceutically effective amount of bryostatin 1 is from about 0.00001 mg/kg to about 5.0 mg/kg per dose.

20. The method of claim 10 wherein the bryostatin 1 is administered at a dose from 0.01-25 µg/m$^2$ IV.

* * * * *